United States Patent
Tagami et al.

(10) Patent No.: US 12,066,593 B2
(45) Date of Patent: Aug. 20, 2024

(54) (METH)ACRYLATE COMPOUND

(71) Applicant: CANON KABUSHIKI KAISHA, Tokyo (JP)

(72) Inventors: Kei Tagami, Kanagawa (JP); Terunobu Saitoh, Tokyo (JP); Akihito Saitoh, Shizuoka (JP); Yota Ito, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 710 days.

(21) Appl. No.: 17/237,474

(22) Filed: Apr. 22, 2021

(65) Prior Publication Data

US 2021/0247546 A1    Aug. 12, 2021

Related U.S. Application Data

(63) Continuation of application No. PCT/JP2019/041609, filed on Oct. 24, 2019.

(30) Foreign Application Priority Data

Oct. 29, 2018  (JP) .................. 2018-203027
Sep. 4, 2019   (JP) .................. 2019-161155

(51) Int. Cl.
*G02B 1/04*  (2006.01)
*C07C 33/26* (2006.01)
(Continued)

(52) U.S. Cl.
CPC .............. *G02B 1/041* (2013.01); *C07C 33/26* (2013.01); *C07C 69/54* (2013.01); *C08F 22/1006* (2020.02); *C09D 133/14* (2013.01)

(58) Field of Classification Search
CPC ......... G02B 1/041; C08F 20/20; C07C 33/26; C07C 69/54; C09D 133/14
See application file for complete search history.

(56) References Cited

U.S. PATENT DOCUMENTS 7,871,755 B2   1/2011  Hattori et al.
9,290,597 B2   3/2016  Saitoh
(Continued)

FOREIGN PATENT DOCUMENTS

JP   2009-80203 A   4/2009
JP   2010-77038 A   4/2010
(Continued)

OTHER PUBLICATIONS

Adrian Woiczechowski-Pop, Ioana L. Dobra, Gheorghe D. Roiban, Anamaria Terec, and Ion Grosu, Synthesis and Structural Analysis of Some Podands With C3 Symmetry, Synthetic Communications1, 42: 3579-3588, 2012 (Year: 2012).*
(Continued)

*Primary Examiner* — Bijan Ahvazi
(74) *Attorney, Agent, or Firm* — Venable LLP

(57) ABSTRACT

The compound having a high refractive index characteristic and a high transmittance is a (meth)acrylate compound represented by the following general formula (1):

(Continued)

in the general formula (1), X represents a phenylene group, $Z_1$ to $Z_3$ are selected from the group consisting of a phenyl group, a heteroaryl group, a phenylene group, a heteroarylene group, a phenylalkylene group having an alkylene group having 1 or more to 4 or less carbon atoms, and a heteroaralkylene group having an alkylene group having 1 or more to 4 or less carbon atoms, $P_1$ to $P_3$ are selected from the group consisting of an acryloyloxy group and a methacryloyloxy group, A is selected from the group consisting of an aryl group, a heteroaryl group, an arylene group, and a heteroarylene group, and "m" and "n" each represent 0 or 1, provided that when the "m" represents 0, the "n" represents 0.

14 Claims, 2 Drawing Sheets

(51) Int. Cl.
  *C07C 69/54* (2006.01)
  *C08F 20/20* (2006.01)
  *C08F 22/10* (2006.01)
  *C09D 133/14* (2006.01)

(56) References Cited

U.S. PATENT DOCUMENTS 10,494,480 B2   12/2019   Nishimura et al.
2020/0012014 A1*  1/2020  Tagami ................ C07D 303/23

FOREIGN PATENT DOCUMENTS

| JP | 2010-215759 A | | 9/2010 | |
| JP | 2010215759 A | * | 9/2010 | .......... C07D 209/86 |
| JP | 2013-112744 A | | 6/2013 | |
| JP | 2013112744 A | * | 6/2013 | .......... C07C 69/653 |
| JP | 2016-26259 A | | 2/2016 | |
| JP | 2018-165355 A | | 10/2018 | |
| WO | 2020/090598 A1 | | 5/2020 | |

OTHER PUBLICATIONS

International Search Report in International Application No. PCT/JP2019/041609 (Jan. 2020).
Informal Comments in International Application No. PCT/JP2019/041609 (Mar. 2020).
Adrian Woiczechowski-Pop et al., "Synthesis and Structural Analysis of Some Podands with C3 Symmetry", 42(22-24) Synthetic Commun. 3579-3588 (2012) (XP055703313).
International Preliminary Report on Patentability in International Application No. PCT/JP2019/041609 (May 2021).
Notice of Reasons for Refusal in Japanese Application No. 2019-161155 (Feb. 2024).
Notice of Reasons for Refusal in Japanese Application No. 2019-161155 (Oct. 2023).

* cited by examiner

(METH)ACRYLATE COMPOUND

CROSS-REFERENCE TO RELATED APPLICATIONS

This application is a Continuation of International Patent Application No. PCT/JP2019/041609 filed Oct. 24, 2019, which claims the benefits of Japanese Patent Application No. 2018-203027, filed Oct. 29, 2018 and Japanese Patent Application No. 2019-161155, filed Sep. 4, 2019, all of which are hereby incorporated by reference herein in their entirety.

BACKGROUND OF THE INVENTION

Field of the Invention

The present disclosure relates to a (meth)acrylate compound.

Description of the Related Art

A resin material having a high refractive index has processability higher than that of a related-art glass material. Accordingly, an investigation has been made on the application of the resin material to a wide variety of fields including a lens for glasses, a lens for a camera or the like, a lens for an optical disc, an fθ lens, an optical element for an image display medium, an optical film, a film, a substrate, various optical filters, a prism, and an optical element for communications.

As the resin material having a high refractive index, in Japanese Patent Application Laid-Open No. 2016-26259, there is a proposal of a photocurable film-forming composition of a triazine ring-containing polymer.

SUMMARY OF THE INVENTION

A cured film described in Japanese Patent Application Laid-Open No. 2016-26259 has a high refractive index, but has involved a problem in that its transmittance is so low that the film cannot be used in, for example, an optical element or a microlens that is required to have a thickness of the order of micrometers.

In view of such background art, an object of the present disclosure is to provide a (meth)acrylate compound having a high refractive index characteristic and a high transmittance.

A (meth)acrylate compound of the present disclosure is represented by the following general formula (1) or (5):

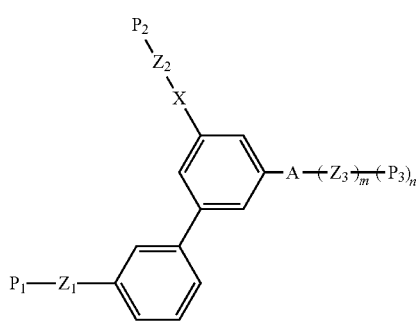

(1)

in the general formula (1), X represents a phenylene group, $Z_1$ to $Z_3$ are each independently selected from the group consisting of a phenyl group, a heteroaryl group, a phenylene group, a heteroarylene group, a phenylalkylene group having an alkylene group having 1 or more to 4 or less carbon atoms, and a heteroaralkylene group having an alkylene group having 1 or more to 4 or less carbon atoms, and the phenyl group, the heteroaryl group, the phenylene group, the heteroarylene group, the phenylalkylene group, and the heteroaralkylene group each represented by any one of the $Z_1$ to the $Z_3$ may each have an alkyl group having 1 or more to 4 or less carbon atoms, $P_1$ to $P_3$ are each independently selected from the group consisting of an acryloyloxy group and a methacryloyloxy group, A is selected from the group consisting of an aryl group, a heteroaryl group, an arylene group, and a heteroarylene group, and "m" and "n" each represent 0 or 1, provided that when the "m" represents 0, the "n" represents 0.

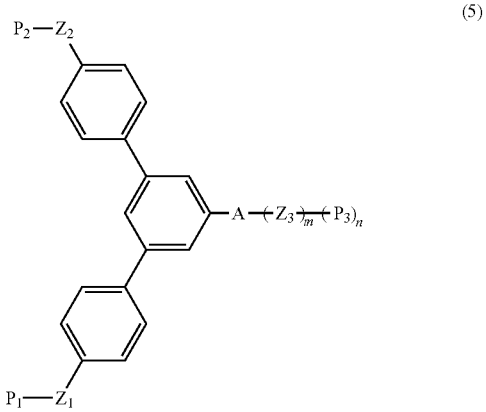

(5)

In the general formula (5), $Z_1$ to $Z_3$ are each independently selected from the group consisting of a phenyl group, a heteroaryl group, a phenylene group, a heteroarylene group, a phenylalkylene group having an alkylene group having 1 or more to 4 or less carbon atoms, and a heteroaralkylene group having an alkylene group having 1 or more to 4 or less carbon atoms, and the phenyl group, the heteroaryl group, the phenylene group, the heteroarylene group, the phenylalkylene group, and the heteroaralkylene group each represented by any one of the $Z_1$ to the $Z_3$ may each have an alkyl group having 1 or more to 4 or less carbon atoms, $P_1$ to $P_3$ are each independently selected from the group consisting of an acryloyloxy group and a methacryloyloxy group, A is selected from the group consisting of an aryl group, a heteroaryl group, an arylene group, and a heteroarylene group, and "m" and "n" each represent 0 or 1, provided that when the "m" represents 0, the "n" represents 0.

Further features of the present disclosure will become apparent from the following description of exemplary embodiments with reference to the attached drawings.

DESCRIPTION OF THE EMBODIMENTS

Figure 1A:
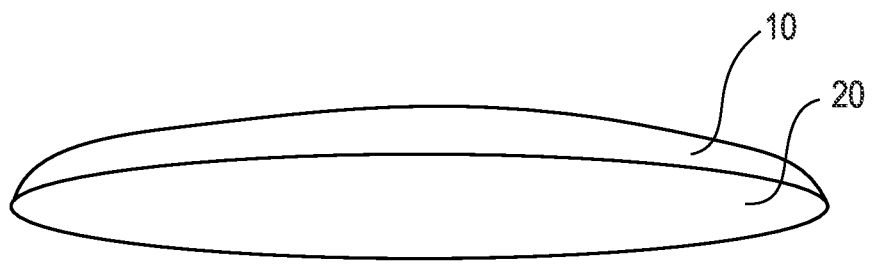
FIG. 1A is a schematic view for illustrating an example of an optical element according to the present disclosure.

The present disclosure is described in detail below by way of embodiments.

<(Meth)Acrylate Compound and Hydroxy Compound>

One aspect of the present disclosure is a (meth)acrylate compound represented by any one of the following general formulae (1) and (5). The term "(meth)acrylate compound" as used herein means an acrylate compound and a methacrylate compound.

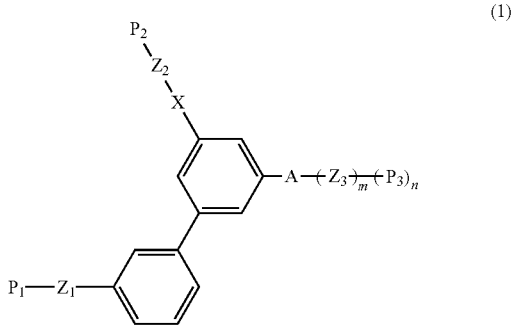
(1)

In the general formula (1), X represents a phenylene group, $Z_1$ to $Z_3$ are each independently selected from the group consisting of a phenyl group, a heteroaryl group, a phenylene group, a heteroarylene group, a phenylalkylene group having an alkylene group having 1 or more to 4 or less carbon atoms, and a heteroaralkylene group having an alkylene group having 1 or more to 4 or less carbon atoms, and the phenyl group, the heteroaryl group, the phenylene group, the heteroarylene group, the phenylalkylene group, and the heteroaralkylene group each represented by any one of the $Z_1$ to the $Z_3$ may each have an alkyl group having 1 or more to 4 or less carbon atoms, $P_1$ to $P_3$ are each independently selected from the group consisting of an acryloyloxy group and a methacryloyloxy group, A is selected from the group consisting of an aryl group, a heteroaryl group, an arylene group, and a heteroarylene group, and "m" and "n" each represent 0 or 1, provided that when the "m" represents 0, the "n" represents 0.

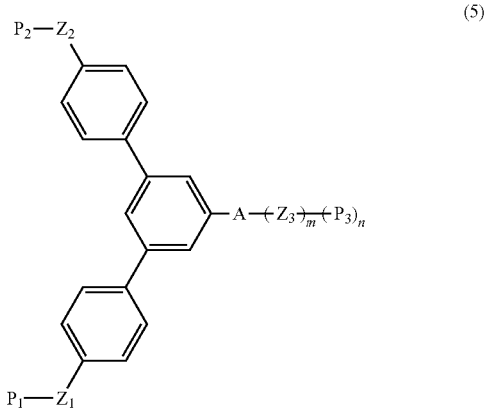
(5)

In the general formula (5), $Z_1$ to $Z_3$ are each independently selected from the group consisting of a phenyl group, a heteroaryl group, a phenylene group, a heteroarylene group, a phenylalkylene group having an alkylene group having 1 or more to 4 or less carbon atoms, and a heteroaralkylene group having an alkylene group having 1 or more to 4 or less carbon atoms, and the phenyl group, the heteroaryl group, the phenylene group, the heteroarylene group, the phenylalkylene group, and the heteroaralkylene group each represented by any one of the $Z_1$ to the $Z_3$ may each have an alkyl group having 1 or more to 4 or less carbon atoms, $P_1$ to $P_3$ are each independently selected from the group consisting of an acryloyloxy group and a methacryloyloxy group, A is selected from the group consisting of an aryl group, a heteroaryl group, an arylene group, and a heteroarylene group, and "m" and "n" each represent 0 or 1, provided that when the "m" represents 0, the "n" represents 0.

Compounds represented by the following general formulae (2) to (4) are each preferred as the (meth)acrylate compound represented by the general formula (1).

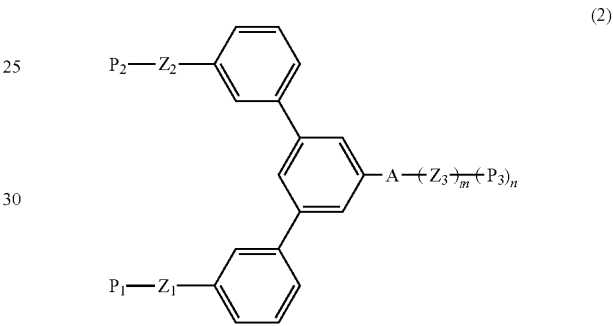
(2)

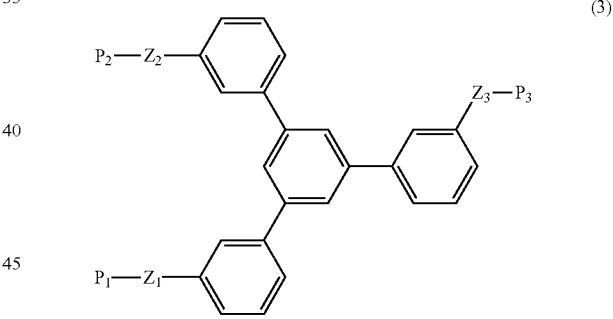
(3)

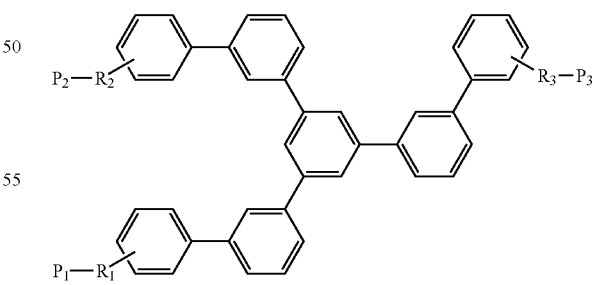
(4)

In the general formula (4), $R_1$ to $R_3$ are each independently selected from the group consisting of alkylene groups each having 1 or more to 4 or less carbon atoms.

The inventors of the present disclosure have made extensive investigations with a view to providing a (meth)acrylate compound having a high refractive index and a high transmittance. As a result, the inventors have found that when the number and bonding positions of the aromatic hydrocarbon rings or aromatic heterocycles of a (meth)acrylate compound are regulated, the compound has a high refractive index and shows a high transmittance. In a trivalent benzene having an aromatic hydrocarbon ring or an aromatic heterocycle bonded to each of its 1-, 3-, and 5-positions, when the benzene has divalent phenylenes bonded to its 1-position and 3-position, and aromatic hydrocarbon rings or aromatic heterocycles bonded to the phenylenes, and the bonding positions of the aromatic hydrocarbon rings or the aromatic heterocycles are adjusted, the benzene shows a high refractive index and a high transmittance. The inventors have found that when at least one of the positions at which the divalent phenylenes and the aromatic hydrocarbon rings or the aromatic heterocycles are bonded to each other is a meta position, or at least two of the bonding positions are identical to each other and are para positions, the benzene has a high refractive index and shows a high transmittance.

In general, a compound having a long conjugated structure typified by an aromatic compound has a band gap smaller than that of a general-purpose material, and hence its absorption edge in a UV light region shifts to a visible light region. Under the influence of the shift, the compound having a long conjugated structure has a high refractive index. However, a practical material is not obtained merely by linking aromatic compounds to build a long conjugated structure. For example, a large aromatic compound involves problems in terms of synthesizability, compatibility with any other compound, and coloring, and a problem in that its transmittance reduces at shorter wavelengths of a visible light region. Accordingly, when the compound is utilized as an optical material, the length of its conjugated structure needs to be adjusted from the viewpoint of improving the transmittance. However, when the conjugated structure of the aromatic compound is shortened or the intermolecular distance thereof is widened by the steric hindrance of a substituent for improving the transmittance, a reduction in refractive index of the compound occurs. The inventors of the present disclosure have considered the (meth)acrylate compound according to the present disclosure having both of a high refractive index and a high transmittance to be as described below. When a trivalent benzene having an aromatic hydrocarbon ring or an aromatic heterocycle bonded to each of its 1-, 3-, and 5-positions has divalent phenylenes bonded to its 1-position and 3-position, and aromatic hydrocarbon rings or aromatic heterocycles bonded to the phenylenes, the benzene shows a high refractive index. The trivalent benzene, the divalent phenylenes, and the aromatic hydrocarbon rings or the aromatic heterocycles may be bonded in a twisted manner for structure stabilization at the time of their bonding. The phenylenes bonded to the 1-position and 3-position of the benzene, and the aromatic hydrocarbon rings or the aromatic heterocycles are bonded in a twisted manner to widen the intermolecular distance of the (meth)acrylate compound. Accordingly, it is assumed that even when the conjugated structure of the (meth)acrylate compound is lengthened, a reduction in transmittance thereof is suppressed, and at the same time, the refractive index thereof can be improved. Further, the introduction of an acryloyloxy group or a methacryloyloxy group that is a polymerizable functional group into the structure reduces the crystallinity of the (meth)acrylate compound to improve its compatibility with any other compound or resin. The inventors have considered that as a result of the foregoing, even when the conjugated structure is extended, the (meth)acrylate compound can show a high refractive index while maintaining a high transmittance.

Examples of the heteroaryl group represented by any one of the $Z_1$ to the $Z_3$ in the general formulae (1) to (5) include, but not limited to, pyrrole, pyridine, pyrazine, and pyrimidine groups.

Examples of the heteroarylene group represented by any one of the $Z_1$ to the $Z_3$ in the general formulae (1) to (5) include, but not limited to, divalent groups each obtained by removing two hydrogen atoms out of the hydrogen atoms directly bonded to a carbon atom or a heteroatom for forming the ring of pyrrole, pyridine, pyrazine, pyrimidine, or the like.

Examples of the heteroarylene group that the heteroaralkylene group represented by any one of the $Z_1$ to the $Z_3$ in the general formulae (1) to (5) has include, but not limited to, divalent groups each obtained by removing two hydrogen atoms out of the hydrogen atoms directly bonded to a carbon atom or a heteroatom for forming the ring of pyrrole, pyridine, pyrazine, pyrimidine, or the like.

Examples of the alkylene group having 1 or more to 4 or less carbon atoms that the phenylalkylene group or the heteroaralkylene group represented by any one of the $Z_1$ to the $Z_3$ in the general formulae (1) to (5) has include a methylene group, an ethylene group, a n-propylene group, an iso-propylene group, and a n-butylene group. Of those, a methylene group, an ethylene group, or a n-propylene group is preferred.

Examples of the alkyl group having 1 or more to 4 or less carbon atoms that the phenylene group, the heteroarylene group, the phenylalkylene group, or the heteroaralkylene group represented by any one of the $Z_1$ to the $Z_3$ in the general formulae (1) to (5) may have include a methyl group, an ethyl group, a n-propyl group, a n-butyl group, and an iso-propyl group. Of those, a methyl group or an ethyl group is more preferred.

Examples of the aryl group represented by the A in the general formulae (1) to (5) include, but not limited to, a phenyl group, a biphenyl group, a terphenyl group, a 1-naphthyl group, and a 2-naphthyl group.

Examples of the arylene group represented by the A in the general formulae (1) to (5) include, but not limited to, a phenylene group, a biphenylene group, a terphenylene group, a 1-naphthylene group, and a 2-naphthylene group.

Examples of the heteroaryl group represented by the A in the general formulae (1) to (5) include, but not limited to, pyrrole, pyridine, pyrazine, and pyrimidine.

Examples of the heteroarylene group represented by the A in the general formulae (1) to (5) include, but not limited to, divalent groups each obtained by removing two hydrogen atoms out of the hydrogen atoms directly bonded to a carbon atom or a heteroatom for forming the ring of pyrrole, pyridine, pyrazine, pyrimidine, or the like.

Examples of the alkylene group having 1 or more to 4 or less carbon atoms represented by any one of the $R_1$ to the $R_3$ in the general formula (4) include a methylene group, an ethylene group, a n-propylene group, an iso-propylene group, and a n-butylene group. Of those, a methylene group, an ethylene group, or a n-propylene group is preferred.

Next, specific examples of the compound according to the present disclosure are shown in Tables 1 to 3, but the present disclosure is not limited thereto.

Table 1 shows examples of such a compound that in the general formula (1), the X and the A each represent a phenylene group, and the bonding positions of the X and the A are meta positions.

TABLE 1
| No. | Z₁ | P1 | X | Z2 |
|---|---|---|---|---|
| T1 | 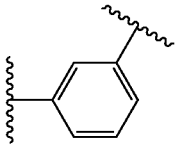 [SMILES: *c1cccc(*)c1] | 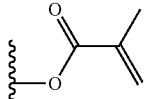 | 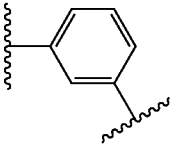 [SMILES: *c1cccc(*)c1] | 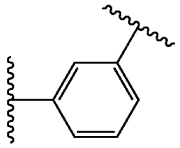 [SMILES: *c1cccc(*)c1] |
| T2 | 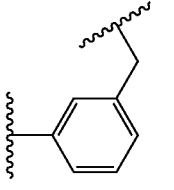 [SMILES: *Cc1cccc(*)c1] | 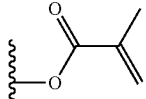 | 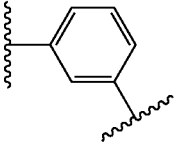 [SMILES: *c1cccc(*)c1] | 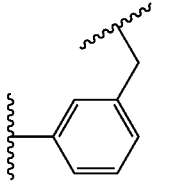 [SMILES: *Cc1cccc(*)c1] |
| T3 | 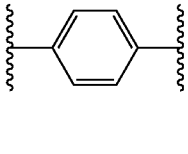 | 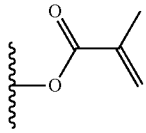 [SMILES: *OC(=O)C(=C)C] | 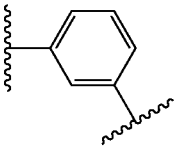 [SMILES: *c1cccc(*)c1] | 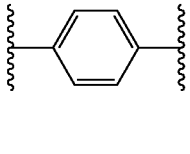 [SMILES: *c1ccc(*)cc1] |
| T4 | 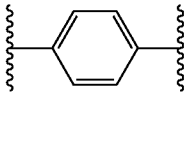 [SMILES: *c1ccc(*)cc1] | 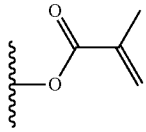 [SMILES: *OC(=O)C(=C)C] | 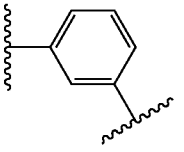 [SMILES: *c1cccc(*)c1] | 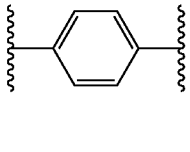 |
| T5 | 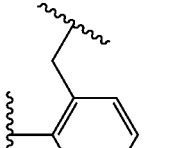 | 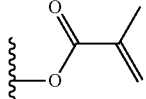 | 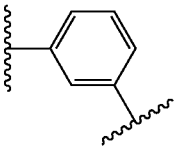 [SMILES: *c1cccc(*)c1] | 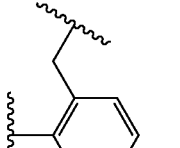 |
| T6 |  | 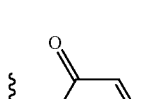 | 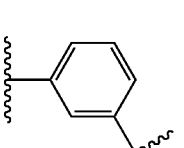 | 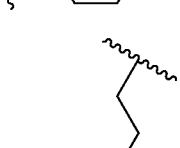 |
| T7 | 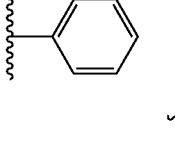 |  | 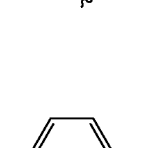 | 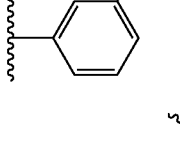 |
| T8 | 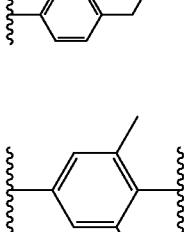 | 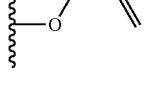 | 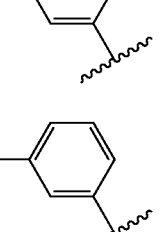 | 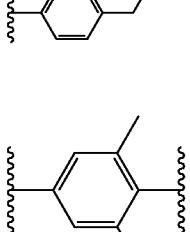 |
| T9 | 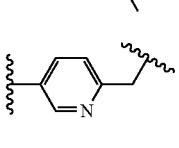 | 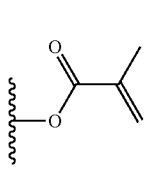 [SMILES: *OC(=O)C(=C)C] | 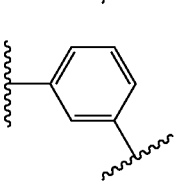 | 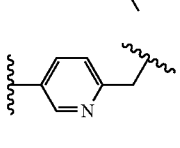 |

TABLE 1-continued
| No. | P2 | A | Z3 | P3 |
|---|---|---|---|---|
| T10 | 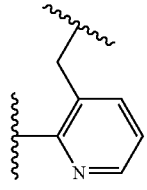 [SMILES: *Cc1cccnc1*] | 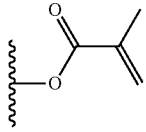 [SMILES: *OC(=O)C(=C)C] | 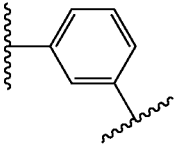 [SMILES: *c1cccc(*)c1] | 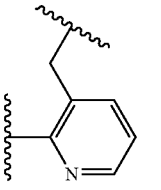 [SMILES: *Cc1cccnc1*] |
| T1 | 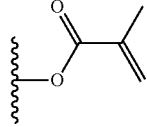 | 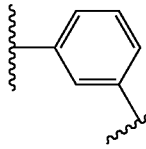 | 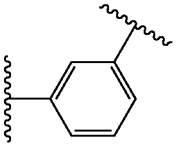 [SMILES: *c1cccc(*)c1] | 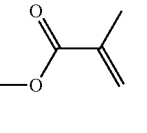 |
| T2 | 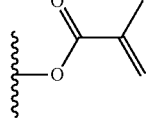 | 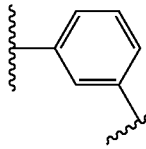 |  | 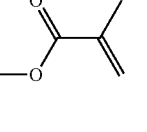 |
| T3 | 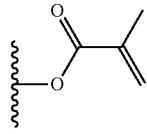 | 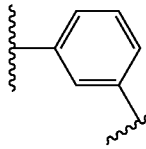 | 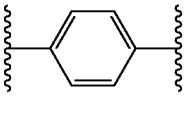 [SMILES: *c1ccc(*)cc1] | 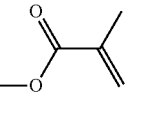 |
| T4 | 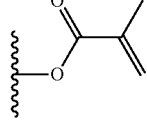 | 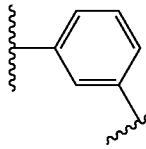 | 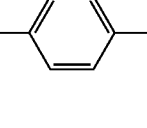 | 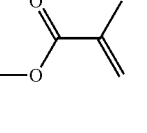 |
| T5 | 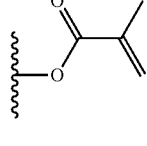 | 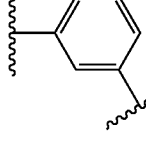 | 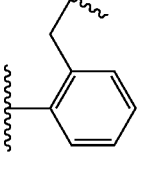 | 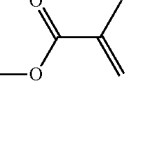 |
| T6 | 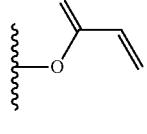 | 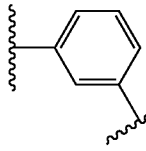 | 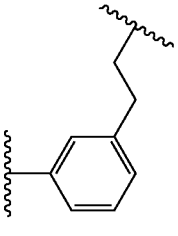 [SMILES: *CCc1cccc(*)c1] | 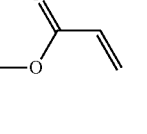 |
| T7 | 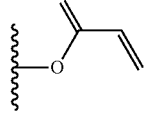 | 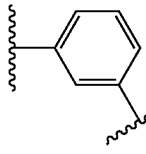 | 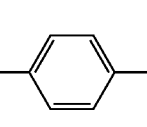 | 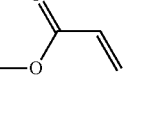 |

TABLE 1-continued

| No. | Z₁ | P₁ | X | Z₂ |
|---|---|---|---|---|
| T8 | methacrylate | m-phenylene | trimethylphenylene | methacrylate |
| T9 | methacrylate | m-phenylene | pyridinediyl | methacrylate |
| T10 | methacrylate | m-phenylene | pyridinediyl | methacrylate |

Table 2 shows examples of such a compound that in the general formula (1), the X represents a phenylene group, and the bonding position of the X is a meta position or an ortho position.

TABLE 2

| No. | Z₁ | P₁ | X | Z₂ |
|---|---|---|---|---|
| T11 | benzyl (m-substituted) | methacrylate | m-phenylene | benzyl (m-substituted) |
| T12 | benzyl (m-substituted) | methacrylate | m-phenylene | benzyl (m-substituted) |
| T13 | benzyl (m-substituted) | methacrylate | m-phenylene | benzyl (m-substituted) |
| T14 | benzyl (m-substituted) | methacrylate | m-phenylene | benzyl (m-substituted) |

TABLE 2-continued

| No. | P2 | A | Z3 | P3 |
|---|---|---|---|---|
| T11 | (methacrylate ester group) | (1,4-phenylene) | (phenyl) | — |

TABLE 2-continued

| | | | | |
|---|---|---|---|---|
| T12 | methacrylate ester | 1,2-phenylene (with extra bond) | | phenyl | — |
| T13 | methacrylate ester | phenyl | — | — |
| T14 | methacrylate ester | pyridin-2-yl | — | — |
| T15 | methacrylate ester | pyrimidin-5-yl | — | — |
| T16 | methacrylate ester | naphthalen-1-yl | — | — |
| T17 | methacrylate ester | naphthalen-2-yl | — | — |
| T18 | methacrylate ester | [1,1':4',1''-terphenyl]-4-yl | — | — |
| T19 | methacrylate ester | 1,4-phenylene | phenyl | — |
| T20 | methacrylate ester | 4,4'-biphenylene | 1,4-phenylene | methacrylate ester |
| T21 | methacrylate ester | 1,4-phenylene | 1,3-phenylene-CH₂- | methacrylate ester |

Table 3 shows examples of the compound represented by the general formula (5).

TABLE 3

| No. | $Z_1$ | $P_1$ | $Z_2$ | $P_2$ |
|-----|-------|-------|-------|-------|
| T22 | meta-phenylene | methacrylate ester | meta-phenylene | methacrylate ester |
| T23 | meta-phenylene-CH₂- | methacrylate ester | meta-phenylene-CH₂- | methacrylate ester |
| T24 | meta-phenylene-CH₂- | methacrylate ester | meta-phenylene-CH₂- | methacrylate ester |
| T25 | meta-phenylene-CH₂- | methacrylate ester | meta-phenylene-CH₂- | methacrylate ester |
| T26 | para-phenylene-(CH₂)₃- | methacrylate ester | para-phenylene-(CH₂)₃- | methacrylate ester |
| T27 | meta-phenylene-(CH₂)₂- | acrylate ester | meta-phenylene-(CH₂)₂- | acrylate ester |
| T28 | 2,4-dimethyl-phenylene | methacrylate ester | 2,4-dimethyl-phenylene | methacrylate ester |
| T29 | meta-phenylene-CH₂- | methacrylate ester | meta-phenylene-CH₂- | methacrylate ester |

TABLE 3-continued

| No. | A | Z3 | P3 |
|---|---|---|---|
| T30 | (benzyl, meta-substituted phenyl) | methacrylate ester | (benzyl, meta-substituted phenyl) | methacrylate ester |
| T31 | (benzyl, meta-substituted phenyl) | methacrylate ester | (benzyl, meta-substituted phenyl) | methacrylate ester |
| T32 | (benzyl, meta-substituted phenyl) | methacrylate ester | (benzyl, meta-substituted phenyl) | methacrylate ester |

| No. | A | Z3 | P3 |
|---|---|---|---|
| T22 | 1,4-phenylene | meta-substituted phenyl | methacrylate ester |
| T23 | 1,4-phenylene | benzyl, meta-substituted phenyl | methacrylate ester |
| T24 | 1,3-phenylene | benzyl, meta-substituted phenyl | methacrylate ester |
| T25 | 1,2-phenylene | benzyl, meta-substituted phenyl | methacrylate ester |
| T26 | 1,4-phenylene | 4-(propyl)phenyl | methacrylate ester |

| | | | |
|---|---|---|---|
| T27 | ![p-phenylene] | ![m-phenyl-CH2CH2] | ![acrylate O-CO-CH=CH2] |
| T28 | ![p-phenylene] | ![trimethylphenylene] | ![methacrylate] |
| T29 | ![phenyl] | — | — |
| T30 | ![pyridyl] | — | — |
| T31 | ![1-naphthyl] | — | — |
| T32 | ![2-naphthyl] | — | — |

A method of producing the (meth)acrylate compound according to the present disclosure is described by way of examples. The method of producing the (meth)acrylate compound of the present disclosure is not limited to a specific production route, and any production method may be adopted. However, a method including using a hydroxy compound represented by the following general formula (6) or (10) as an intermediate is preferred.

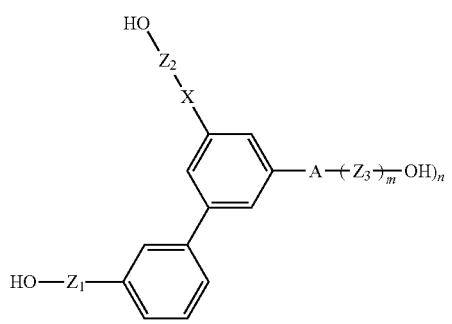

(6)

In the general formula (6), X represents a phenylene group, $Z_1$ to $Z_3$ are each independently selected from the group consisting of a phenyl group, a heteroaryl group, a phenylene group, a heteroarylene group, a phenylalkylene group having an alkylene group having 1 or more to 4 or less carbon atoms, and a heteroaralkylene group having an alkylene group having 1 or more to 4 or less carbon atoms, and the phenyl group, the heteroaryl group, the phenylene group, the heteroarylene group, the phenylalkylene group, and the heteroaralkylene group each represented by any one of the $Z_1$ to the $Z_3$ may each have an alkyl group having 1 or more to 4 or less carbon atoms, A is selected from the group consisting of an aryl group, a heteroaryl group, an arylene group, and a heteroarylene group, and "m" and "n" each represent 0 or 1, provided that when the "m" represents 0, the "n" represents 0.

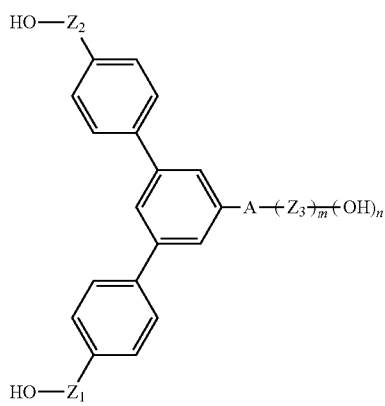

(10)

In the general formula (10), $Z_1$ to $Z_3$ are each independently selected from the group consisting of a phenyl group, a heteroaryl group, a phenylene group, a heteroarylene group, a phenylalkylene group having an alkylene group having 1 or more to 4 or less carbon atoms, and a heteroaralkylene group having an alkylene group having 1 or more to 4 or less carbon atoms, and the phenyl group, the heteroaryl group, the phenylene group, the heteroarylene group, the phenylalkylene group, and the heteroaralkylene group each represented by any one of the $Z_1$ to the $Z_3$ may each have an alkyl group having 1 or more to 4 or less carbon atoms, A is selected from the group consisting of an aryl group, a heteroaryl group, an arylene group, and a heteroarylene group, and "m" and "n" each represent 0 or 1, provided that when the "m" represents 0, the "n" represents 0.

Compounds represented by the following general formulae (7) to (9) are each preferred as the hydroxy compound represented by the general formula (6).

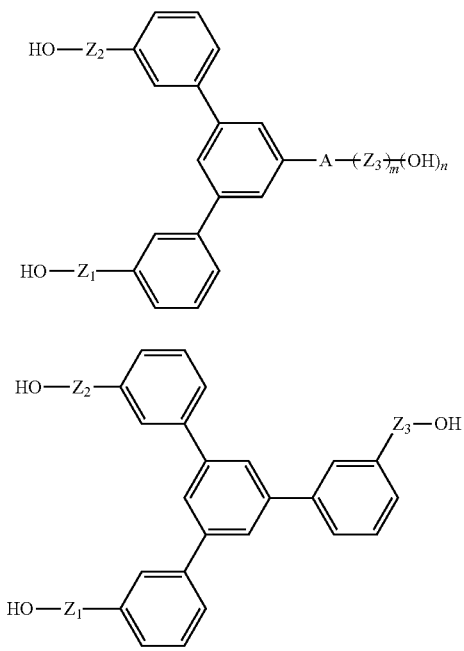

(7)

(8)

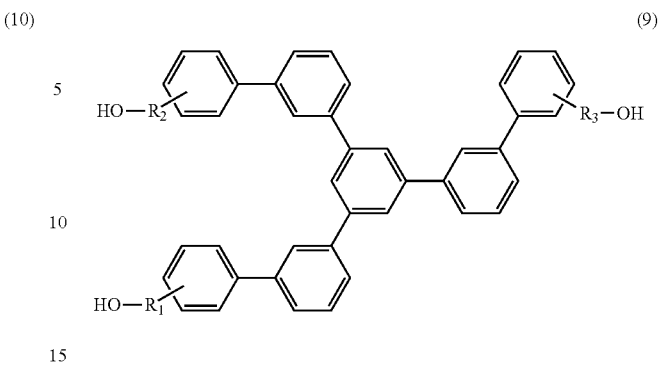

(9)

In the general formula (9), $R_1$ to $R_3$ are each independently selected from the group consisting of alkylene groups each having 1 or more to 4 or less carbon atoms.

Specific examples of the $Z_1$ to the $Z_3$, the A, and the $R_1$ to the $R_3$ in the general formulae (6) to (10) are the same as those described for the general formulae (1) to (5).

The (meth)acrylate compound represented by any one of the general formulae (1) to (5) and the hydroxy compound represented by any one of the general formulae (6) to (10) in the present disclosure can be synthesized by using known synthesis methods. Synthesis routes are represented below. In the following synthesis routes, for example, Z represents "-Ph-CH$_2$—" and P represents "—O—C(=O)—CH=CH$_2$". However, the production method of the present disclosure is not limited thereto. For example, a method including directly introducing an acryloyloxy group or a methacryloyloxy group into an intermediate except the hydroxy compound represented by the general formula (6) or (10) may be adopted.

Synthesis route 1-1

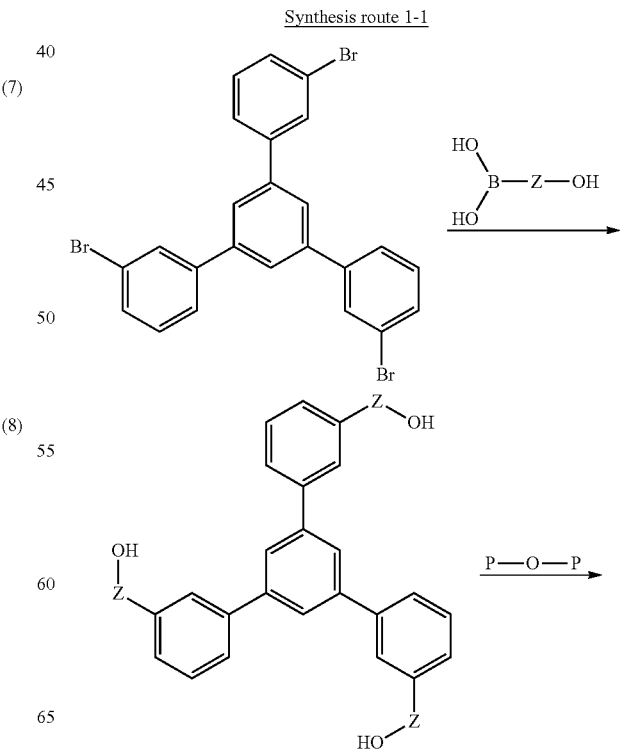

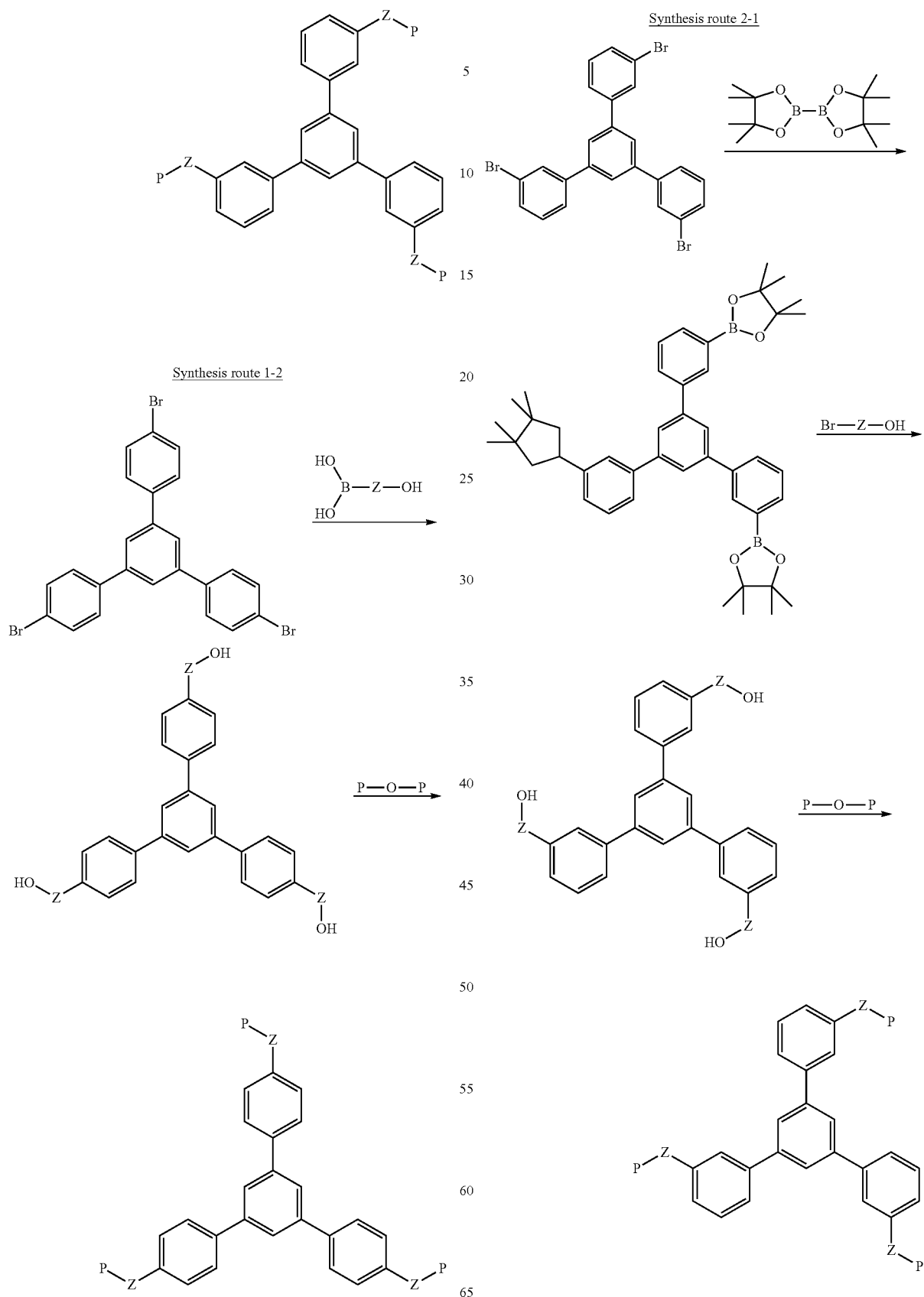

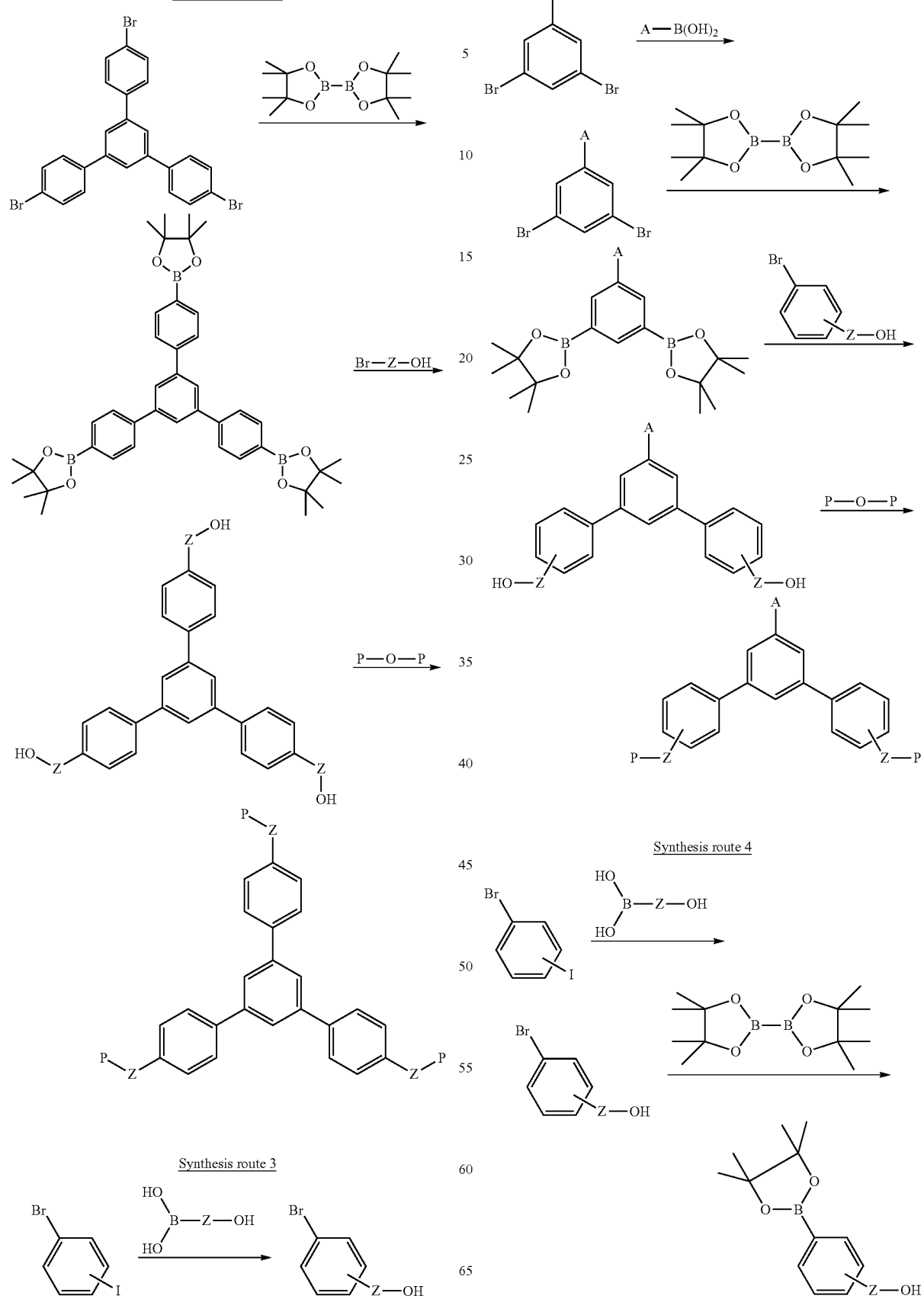

-continued

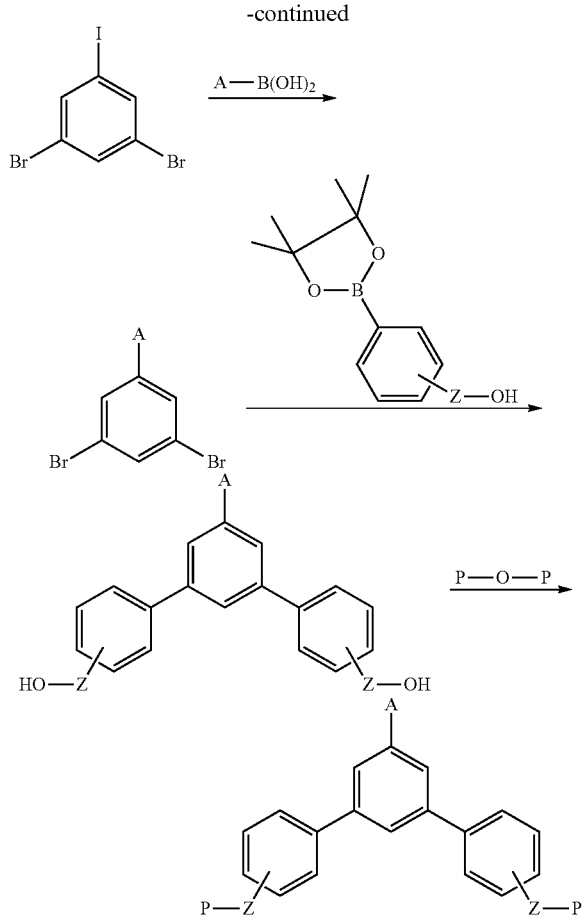

The coupling reaction based on the metal catalyst may be arbitrarily selected and used. For example, the Ullmann reaction involving utilizing copper, the Buchwald-Hartwig reaction involving utilizing an amine or the like, the Suzuki coupling involving utilizing boric acid or the like, the Stille coupling involving utilizing an organotin, or the Negishi coupling involving utilizing an organozinc is suitably used as a typical method.

The (meth)acrylation reaction may be arbitrarily selected. For example, a method involving esterifying a hydroxy group with a (meth)acrylic acid halide or (meth)acrylic anhydride, an ester exchange reaction involving using a lower alcohol ester of (meth)acrylic acid, a direct esterification reaction involving subjecting (meth)acrylic acid and the diol to dehydration condensation through the use of a dehydration condensation agent, such as N,N'-dicyclohexylcarbodiimide, or a method involving heating (meth)acrylic acid and the diol in the presence of a dehydrating agent, such as sulfuric acid, is suitably used as a typical method.

<Resin Composition and Resin Cured Product>

A resin composition according to the present disclosure includes the above-mentioned (meth)acrylate compound of the present disclosure. In addition, a resin cured product of the present disclosure is a molded body obtained by polymerizing the resin composition of the present disclosure. The resin composition according to the present disclosure may include one kind of (meth)acrylate compound, or may include a plurality of kinds of (meth)acrylate compounds. That is, the resin cured product according to the present disclosure may be a homopolymer of the (meth)acrylate compound represented by any one of the general formulae (1) to (5), or may be a copolymer of such compounds.

In addition, a polymerization inhibitor may be used as required so that the polymerization of the (meth)acrylate compound of the present disclosure may not advance at the time of a reaction for the production of the compound or at the time of its storage. Examples of the polymerization inhibitor may include: hydroquinones, such as p-benzoquinone, hydroquinone, hydroquinone monomethyl ether, and 2,5-diphenyl-p-benzoquinone; N-oxy radicals, such as tetramethylpiperidinyl-N-oxy radical (TEMPO); substituted catechols, such as t-butylcatechol; amines, such as phenothiazine, diphenylamine, and phenyl-β-naphthylamine; nitrosobenzene; picric acid; molecular oxygen; sulfur; and copper(II) chloride. Of those, hydroquinones, phenothiazine, and N-oxyradicals are preferred from the viewpoints of a general-purpose property and the suppression of the polymerization, and hydroquinones are particularly preferred.

A lower limit for the usage amount of the polymerization inhibitor is typically 10 ppm or more, preferably 50 ppm or more with respect to the (meth)acrylate compound, and an upper limit therefor is typically 10,000 ppm or less, preferably 1,000 ppm or less with respect thereto. In the case where the usage amount is excessively small, the following risk arises: the effect of the polymerization inhibitor is not expressed or the effect is small even when the effect is expressed, and hence the polymerization advances at the time of the reaction or at the time of condensation in a posttreatment step. In contrast, when the usage amount is excessively large, the following risk arises: the polymerization inhibitor serves as, for example, an impurity at the time of the production of a resin composition to be described later, and has an adverse effect, such as the inhibition of the polymerization reactivity of the (meth)acrylate compound.

The resin composition according to the present disclosure is preferably formed of a composition containing the (meth)acrylate compound of the present disclosure, a polymerization initiator, and the polymerization inhibitor, and as required, a photosensitizer, a heat stabilizer, a light stabilizer, an antioxidant, a resin, or a monomer.

The content of the (meth)acrylate compound to be incorporated into the resin composition of the present disclosure is desirably 1.0 mass % or more to 99 mass % or less, preferably 50 mass % or more to 99 mass % or less with respect to the entirety of the resin composition.

Examples of the polymerization initiator include, but are not limited to, a polymerization initiator that generates a radical species or a cation species through light irradiation, and a polymerization initiator that generates a radical species with heat.

Examples of the polymerization initiator that generates a radical species through light irradiation include, but not limited to, 2-benzyl-2-dimethylamino-1-(4-morpholinophenyl)-1-butanone, 1-hydroxycyclohexyl phenyl ketone, 2-hydroxy-2-methyl-1-phenyl-propan-1-one, bis(2,4,6-trimethylbenzoyl)-phenylphosphine oxide, 4-phenylbenzophenone, 4-phenoxybenzophenone, 4,4'-diphenylbenzophenone, and 4,4'-diphenoxybenzophenone.

In addition, suitable examples of the polymerization initiator that generates a cation species through light irradiation include, but not limited to, polymerization initiators such as iodonium (4-methylphenyl)[4-(2-methylpropyl)phenyl]-hexafluorophosphate.

Further, examples of the polymerization initiator that generates a radical species with heat include, but not limited to: azo compounds, such as azobisisobutyronitrile (AIBN);

and peroxides, such as benzoyl peroxide, t-butyl peroxypivalate, t-butyl peroxyneohexanoate, t-hexyl peroxyneohexanoate, t-butyl peroxyneodecanoate, t-hexyl peroxyneodecanoate, cumyl peroxyneohexanoate, and cumyl peroxyneodecanoate.

When UV light or the like is applied as light to initiate the polymerization of the resin composition, a known sensitizer or the like may be used. Typical examples of the sensitizer include, but not limited to, benzophenone, 4,4-diethylaminobenzophenone, 1-hydroxycyclohexyl phenyl ketone, isoamyl p-dimethylaminobenzoate, methyl 4-dimethylaminobenzoate, benzoin, benzoin ethyl ether, benzoin isobutyl ether, benzoin isopropyl ether, 2,2-diethoxyacetophenone, methyl o-benzoylbenzoate, 2-hydroxy-2-methyl-1-phenyl-propan-1-one, and acylphosphine oxides.

The addition ratio of the polymerization initiator, such as a photopolymerization initiator, with respect to a polymerizable resin component may be appropriately selected in accordance with a light irradiation amount and an additional heating temperature. In addition, the addition ratio may be adjusted in accordance with the target average molecular weight of a polymer to be obtained. The addition amount of the polymerization initiator, such as a photopolymerization initiator, to be used in the polymerization (curing) and molding of the resin composition according to the present disclosure preferably falls within the range of from 0.01 mass % or more to 10.00 mass % or less with respect to the polymerizable resin component. The polymerization initiators, such as photopolymerization initiators, may be used alone or in combination thereof in accordance with the reactivity of the resin and the wavelength of the light to be applied.

The light stabilizer is not particularly limited as long as the light stabilizer does not have a large influence on the optical characteristics of the molded body, and typical examples thereof may include: benzotriazole-based materials, such as 2-(2H-benzotriazol-2-yl)-p-cresol, 2-(2H-benzotriazol-2-yl)-4,6-bis(1-methyl-1-phenylethyl)phenol, 2-[5-chloro(2H)-benzotriazol-2-yl-4-methyl-6-(tert-butyl)]phenol, 2-(2H-benzotriazol-2-yl)-4,6-di-tert-pentylphenol, 2-(2H-benzotriazol-2-yl)-4-(1,1,3,3-tetramethylbutyl)phenol, 2,2'-methylenebis[6-(2H-benzotriazol-2-yl)-4-(1,1,3,3-tetramethylbutyl)]phenol, and 2-(2H-benzotriazol-2-yl)-6-dodecyl-4-methylphenol; cyanoacrylate-based materials, such as ethyl 2-cyano-3,3-diphenylacrylate and 2-ethylhexyl 2-cyano-3,3-diphenylacrylate; triazine-based materials; and benzophenone-based materials, such as octabenzone and 2,2'-4,4'-tetrahydrobenzophenone. The light stabilizer may also serve as the photosensitizer, and in that case, the photosensitizer may not be added. The addition amount of the light stabilizer to be used in the polymerization (curing) and molding of the resin composition of the present disclosure preferably falls within the range of from 0.01 mass % or more to 10.00 mass % or less with respect to the total amount of the polymerizable resin component.

The heat stabilizer is not particularly limited as long as the heat stabilizer does not have a large influence on the optical characteristics of the molded body, and for example: pentaerythritol tetrakis[3-(3,5-di-tert-butyl-4-hydroxyphenyl)]propionate, octadecyl-3-(3,5-di-tert-butyl-4-hydroxyphenyl)propionate, 3,5-bis(1,1-dimethylethyl)-4-hydroxybenzenepropanoic acid, and C7-C9 side chain alkyl esters; hindered phenol-based materials, such as 4,6-bis(octylthiomethyl)-o-cresol, 4,6-bis(dodecylthiomethyl)-o-cresol, ethylenebis(oxyethylene)bis[3-(5-tert-butyl-4-hydroxy-m-tolyl)]propionate, and hexamethylenebis[3-(3,5-di-tert-butyl-4-hydroxyphenyl)]propionate; phosphorus-based materials, such as tris(2,4-di-tert-butylphenyl) phosphite; and sulfur-based materials, such as dioctadecyl 3,3'-thiodipropionate, may be used. The addition amount of the heat stabilizer to be used in the polymerization (curing) and molding of the resin composition of the present disclosure preferably falls within the range of from 0.01 mass % or more to 10.00 mass % or less with respect to the total amount of the polymerizable resin component.

The antioxidant is not particularly limited as long as the antioxidant does not have a large influence on the optical characteristics of the molded body, and typical examples thereof include hindered amine-based materials, such as bis(2,2,6,6-tetramethyl-4-piperidyl) sebacate and bis(1,2,2,6,6-pentamethyl-4-piperidyl)[[3,5-bis(1,1-dimethylethyl)-4-hydroxyphenyl]methyl]butyl malonate. The addition amount of the antioxidant to be used in the polymerization (curing) and molding of the resin composition according to the present disclosure preferably falls within the range of from 0.01 mass % or more to 10.00 mass % or less with respect to the total amount of the polymerizable resin component.

The resin or the monomer that may be utilized in the resin composition according to the present disclosure is not particularly limited. Examples thereof include, but not limited to: (meth)acrylate compounds, such as 1,3-adamantanediol dimethacrylate, 1,3-adamantanedimethanol dimethacrylate, tricyclodecanedimethanol diacrylate, pentaerythritol tetraacrylate, propoxylated neopentyl glycol diacrylate, dipropylene glycol diacrylate, ethoxylated bisphenol A dimethacrylate, tris(2-hydroxyethyl) isocyanurate triacrylate, 2-(2-ethoxyethoxy)ethyl acrylate, stearyl acrylate, tetrahydrofurfuryl acrylate, 2-phenoxyethyl acrylate, isodecyl acrylate, isobornyl acrylate, isobornyl methacrylate, 1,3-butylene glycol diacrylate, 1,4-butanediol diacrylate, diethylene glycol diacrylate, 1,6-hexanediol diacrylate, triethylene glycol diacrylate, tripropylene glycol diacrylate, dipropylene glycol diacrylate, triethylene glycol dimethacrylate, ethylene glycol dimethacrylate, tetraethylene glycol dimethacrylate, 1,4-butanediol dimethacrylate, diethylene glycol dimethacrylate, 1,6-hexanediol dimethacrylate, tripropylene glycol dimethacrylate, dipropylene glycol dimethacrylate, trimethylol propane trimethacrylate, 9,9-bis[4-(2-acryloyloxyethoxy)phenyl]fluorene, 9,9-bis[4-(2-methacryloyloxyethoxy)phenyl]fluorene, 9,9-bis[4-(2-acryloyloxy)phenyl]fluorene, 9,9-bis[4-(2-methacryloyloxy)phenyl]fluorene, benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidyl methacrylate, phenoxyethyl acrylate, phenoxyethyl methacrylate, phenyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol diacrylate, polyethylene glycol dimethacrylate, neopentyl glycol diacrylate, neopentyl glycol dimethacrylate, ethylene glycol bisglycidyl acrylate, ethylene glycol bisglycidyl methacrylate, bisphenol A diacrylate, bisphenol A dimethacrylate, 2,2-bis(4-acryloxyethoxyphenyl)propane, 2,2-bis(4-methacryloxyethoxyphenyl)propane, 2,2-bis(4-acryloxydiethoxyphenyl)propane, 2,2-bis(4-methacryloxydiethoxyphenyl)propane, bisphenol F diacrylate, bisphenol F dimethacrylate, 1,1-bis(4-acryloxyethoxyphenyl)methane, 1,1-bis(4-methacryloxyethoxyphenyl)methane, 1,1-bis(4-acryloxydiethoxyphenyl)methane, 1,1-bis(4-methacryloxydiethoxyphenyl)methane, 1,1-bis(4- acryloxyethoxyphenyl)sulfone, 1,1-bis(4-methacryloxyethoxyphenyl)sulfone, 1,1-bis(4-acryloxydiethoxyphenyl)sulfone, 1,1-bis(4-methacryloxydiethoxyphenyl)sulfone, dimethylol tricyclodecane diacrylate, trimethylol propane triacrylate, trimethylolpropane trimethacrylate, glycerol diacrylate, glycerol dimethacrylate, pentaerythritol triacrylate, pentaerythritol tetraacrylate, pentaerythritol tetramethacrylate, methyl thioacrylate, methyl thiomethacrylate, phenyl thioacrylate, benzyl thiomethacrylate, xylylene dithiol diacrylate, xylylene dithiol dimethacrylate, mercaptoethyl sulfide diacrylate, and mercaptoethyl sulfide dimethacrylate; allyl compounds, such as allyl glycidyl ether, diallyl phthalate, diallyl terephthalate, diallyl isophthalate, diallyl carbonate, and diethylene glycol bisallyl carbonate; vinyl compounds, such as styrene, chlorostyrene, methylstyrene, bromostyrene, dibromostyrene, divinylbenzene, and 3,9-divinylspirobi(m-dioxane); and diisopropenylbenzene.

In addition, the resin or the monomer may be a thermoplastic resin. Examples thereof include: polyolefin-based resins, such as an ethylene homopolymer, a random or block copolymer of ethylene and one or two or more kinds of α-olefins, such as propylene, 1-butene, 1-pentene, 1-hexene, and 4-methyl-1-pentene, a random or block copolymer of ethylene and one or two or more kinds of vinyl acetate, acrylic acid, methacrylic acid, methyl acrylate, and methyl methacrylate, a propylene homopolymer, a random or block copolymer of propylene and one or two or more kinds of α-olefins except propylene, such as 1-butene, 1-pentene, 1-hexene, and 4-methyl-1-pentene, a 1-butene homopolymer, an ionomer resin, and a mixture of those polymers; hydrocarbon atom-based resins, such as a petroleum resin and a terpene resin; polyester-based resins, such as polyethylene terephthalate, polybutylene terephthalate, and polyethylene naphthalate; polyamide-based resins, such as nylon 6, nylon 66, nylon 11, nylon 12, nylon 610, nylon 6/66, nylon 66/610, and nylon MXD; acrylic resins, such as polymethyl methacrylate; styrene- or acrylonitrile-based resins, such as polystyrene, a styrene-acrylonitrile copolymer, a styrene-acrylonitrile-butadiene copolymer, and polyacrylonitrile; polyvinyl alcohol-based resins, such as polyvinyl alcohol and an ethylene-vinyl alcohol copolymer; polycarbonate resins; polyketone resins; polymethylene oxide resins; polysulfone resins; polyimide resins; and polyamide imide resins. Those resins or monomers may be used alone or as a mixture thereof.

The content of the resin or the monomer to be incorporated into the resin composition according to the present disclosure is desirably 0.01 mass % or more to 99 mass % or less, and is preferably 0.01 mass % or more to 50 mass % or less in consideration of the refractive index characteristic of the resin composition to be obtained and the brittleness of the molded body.

<Optical Element>

Figure 1B:
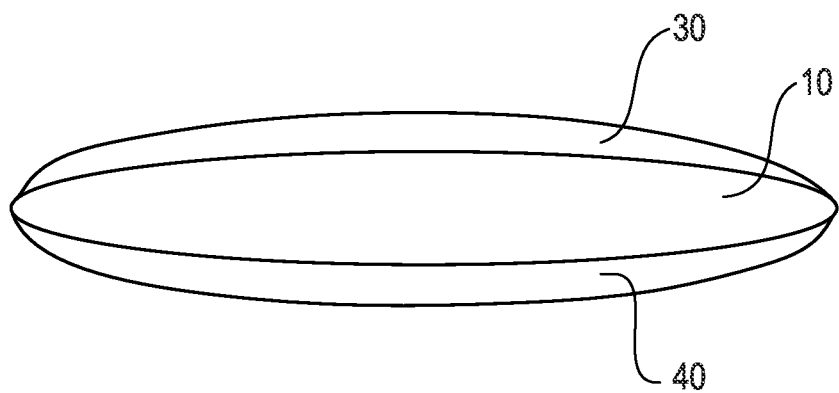
FIG. 1B is a schematic view for illustrating another example of the optical element according to the present disclosure.

FIG. 1A and FIG. 1B are each a schematic view for illustrating an example of an optical element of the present disclosure. In the optical element of FIG. 1A, a thin film 10 that is a resin cured product obtained by curing the resin composition is arranged on one surface of a glass substrate 20 that is a base material. For example, a method including forming a layer structure having a small thickness on a base material having optical transparency is adopted as a method of producing the optical element of FIG. 1A. Specifically, a mold formed of a metal is arranged so as to have a certain distance from the base material, and a gap present between the mold and the base material is filled with the resin composition that is fluid. After that, mold molding is performed by lightly pressing down the mold. Then, the resin composition is polymerized while being kept in the state as required.

Light irradiation to be used in such polymerization reaction is performed by using light having a suitable wavelength, typically UV light or visible light in correspondence with a mechanism resulting from radical formation involving using a photopolymerization initiator. For example, raw materials, such as the monomers of the resin composition subjected to the die molding, are uniformly irradiated with the light through the light-transmitting material to be utilized as the base material, specifically the glass substrate. An irradiation light amount is appropriately selected in accordance with the mechanism resulting from the radical formation involving utilizing the photopolymerization initiator and with the content of the photopolymerization initiator to be incorporated. Meanwhile, in such production of the molded body of the resin cured product by a photopolymerization reaction, it is more preferred that the entirety of the raw materials, such as the monomers, subjected to the die molding be uniformly irradiated with the irradiation light. Accordingly, it is more preferred to select light having such a wavelength that the light irradiation to be utilized can be uniformly performed through the light-transmitting material to be utilized as the base material, such as the glass substrate. At this time, a reduction in thickness of the resin cured product to be formed on the base material of the light-transmitting material is more suitable for the present disclosure.

In the optical element of FIG. 1B, the thin film 10 that is a resin cured product is arranged between a glass substrate 30 and a glass substrate 40 that are base materials. A method of producing the optical element of FIG. 1B is, for example, as described below. An uncured resin composition or the like is poured into a gap between the two base materials, and is molded by being lightly pressed down. Then, the photopolymerization of the uncured resin composition is performed while the composition is kept in the state. Thus, the optical element in which the resin cured product is sandwiched between the base materials can be obtained.

Similarly, the resin cured product may be produced by a thermal polymerization method. In this case, it is desired that the temperature of the entirety of the composition be further uniformized, and a reduction in total thickness of the resin cured product to be formed on the base material of the light-transmitting material is more suitable for the present disclosure. In addition, when the total thickness of the resin cured product to be formed is increased, an irradiation amount, an irradiation intensity, a light source, and the like need to be selected while the thickness, the absorption of a resin component, and the absorption of a fine particle component are further considered.

<Image Pickup Apparatus>

Figure 2:
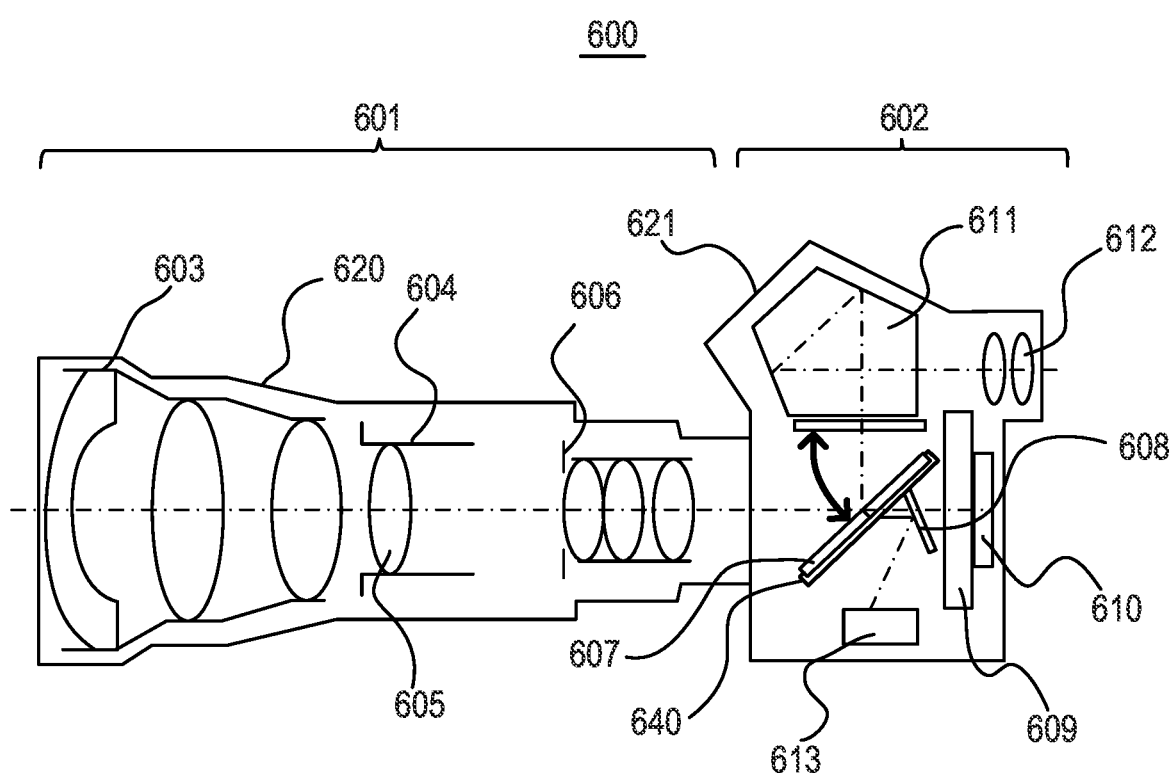
FIG. 2 is a schematic view for illustrating an example of an image pickup apparatus according to the present disclosure.

FIG. 2 is a schematic sectional view for illustrating an example of an image pickup apparatus according to an exemplary embodiment of the present disclosure, and is an illustration of the configuration of a single-lens reflex digital camera having bonded thereto a lens barrel (interchangeable lens) that is an example of an optical apparatus of the present disclosure. The optical apparatus of the present disclosure refers to an apparatus including an optical system including the optical element of the present disclosure, such as a pair of binoculars, a microscope, a semiconductor-exposing apparatus, or an interchangeable lens. Alternatively, the optical apparatus refers to an apparatus configured to produce an image with light that has passed the optical element of the present disclosure.

In addition, the image pickup apparatus of the present disclosure refers to an electronic apparatus including an image pickup element configured to receive light that has passed the optical element of the present disclosure, such as: a camera system, such as a digital still camera or a digital video camera; or a cellular phone. A module-shaped form to be mounted on an electronic apparatus, such as a camera module, may be included in the image pickup apparatus.

In FIG. 2, a camera 600 according to this embodiment is obtained by bonding a camera main body 602 and a lens barrel 601 that is an optical apparatus, and the lens barrel 601 is a so-called interchangeable lens removably mounted onto the camera main body 602.

Light from an object passes an optical system formed of, for example, a plurality of lenses 603 and 605 arranged on the optical axis of an image taking optical system in the housing 620 of the lens barrel 601, and is received by an image pickup element. The optical element of the present disclosure may be used in, for example, any one of the lenses 603 and 605. Herein, the lens 605 is supported by an inner cylinder 604, and is movably supported with respect to the outer cylinder of the lens barrel 601 for focusing or zooming.

During an observation period before image taking, the light from the object is reflected by a main mirror 607 in the housing 621 of the camera main body to permeate a prism 611, and then a taken image is projected to a photographer through a finder lens 612. The main mirror 607 is, for example, a half mirror, and light that has permeated the main mirror is reflected by a submirror 608 toward an autofocus (AF) unit 613. The reflected light is used in, for example, ranging. In addition, the main mirror 607 is mounted on and supported by a main mirror holder 640 through adhesion or the like. At the time of the image taking, the main mirror 607 and the submirror 608 are moved to the outside of an optical path via a driving mechanism (not shown) to open a shutter 609, thereby forming a taken light image that has entered from the lens barrel 601 on an image pickup element 610. In addition, a diaphragm 606 is configured so as to be capable of changing brightness and a focal depth at the time of the image taking through a change in aperture area thereof.

EXAMPLES

The present disclosure is described in more detail below by way of Examples. However, the present disclosure is by no means limited by Examples described below as long as the other examples do not depart from the gist of the present disclosure. A synthesized product was analyzed with a NMR apparatus (JNM-ECA400 (product name) manufactured by JEOL Ltd.).

Example 1 (Production of Compound Example T2)

(1) Synthesis of T2 Intermediate

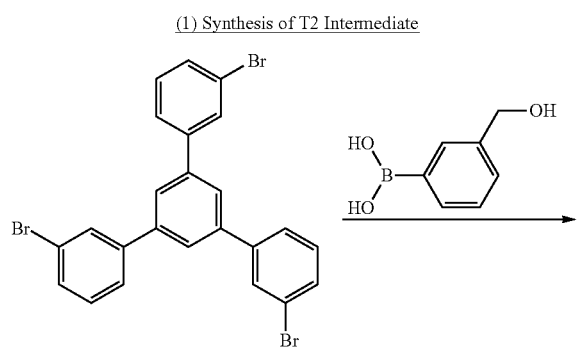

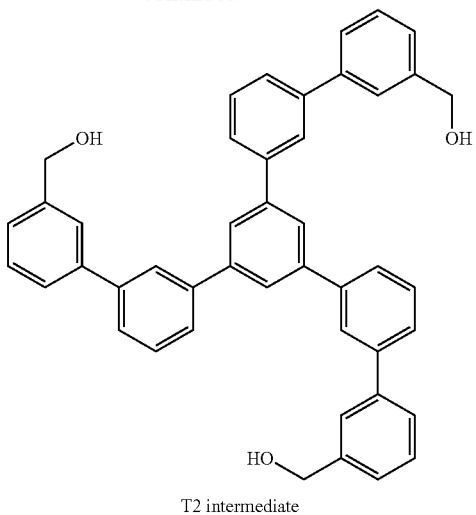

T2 intermediate

Under a nitrogen atmosphere, 10.0 g of 1,3,5-tris(3-bromophenyl)benzene, 9.3 g of 3-(hydroxymethyl)phenylboronic acid, 9.73 g of sodium carbonate, 0.042 g of palladium acetate, 0.18 g of 2-dicyclohexylphosphino-2',4',6'-triisopropylbiphenyl, 240 mL of toluene, 80 mL of ethanol, and 80 mL of water were loaded into a 1,000-milliliter three-necked flask, and were refluxed and stirred for 8 hours under heating. After the heating, the mixture was left to cool to room temperature. After that, 100 mL of hexane was added to the mixture, and the whole was stirred for 1 hour, followed by filtration. The resultant cake was washed with water and hexane, and was then dissolved in acetone. 10.0 Grams of activated carbon was added to the solution, and the mixture was stirred under room temperature for 30 minutes. After that, the mixture was filtered, and the solvent of the filtrate was removed. The crude product obtained by removing the solvent was washed with ethanol and dried to provide 6.2 g of a T2 intermediate (yield: 54%). The structure of the resultant product was identified by 1H-NMR.

1H-NMR (CDCl$_3$): δ 1.83 (br, 3H), 4.80 (s, 6H), 7.39 (d, 3H), 7.48 (t, 3H), 7.58 (t, 3H), 7.61-7.63 (m, 3H), 7.64-7.66 (m, 3H), 7.70-7.74 (m, 6H), 7.92 (s, 3H), 7.94 (t, 3H)

(2) Synthesis of T2

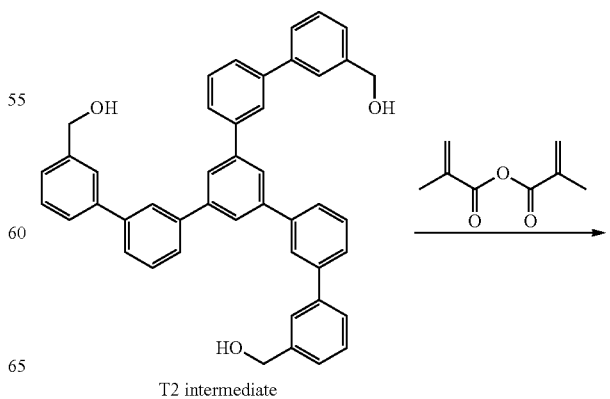

T2 intermediate

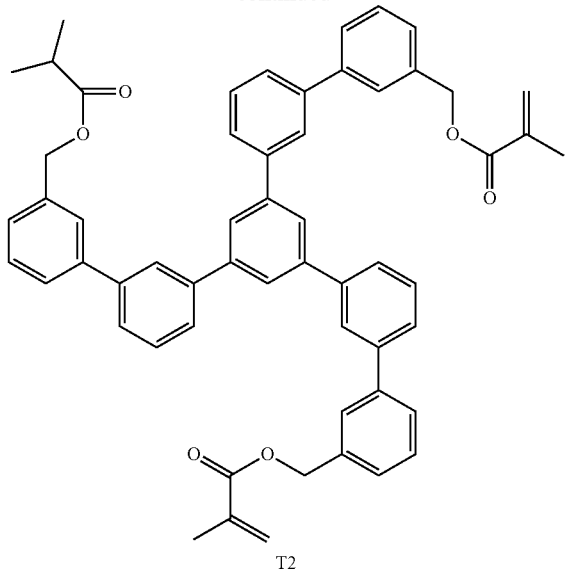

T2

Under a nitrogen atmosphere, 6.0 g of the T2 intermediate, 210 mL of tetrahydrofuran, 0.36 g of hydroquinone monomethyl ether (MEHQ), and 5.5 mL of triethylamine were loaded into a 500-milliliter three-necked flask. After that, 4.9 g of methacrylic anhydride was dropped into the flask, and the mixture was refluxed and stirred for 20 hours under heating. The reaction liquid was diluted with toluene, and the resultant organic layer was washed with acidic and basic aqueous solutions. After that, the organic layer was dried with brine and anhydrous magnesium sulfate. The crude product obtained by removing the solvent was purified by silica gel chromatography to provide 3.6 g of the T2 (yield: 45%). The structure of the product was identified by 1H-NMR.

$^1$H-NMR (CDCl$_3$): δ 1.98 (t, 9H), 5.20 (s, 6H), 5.58 (dt, 3H), 6.18 (dt, 3H), 7.41 (d, 3H), 7.49 (t, 3H), 7.59 (t, 3H), 7.64-7.66 (m, 9H), 7.72-7.74 (m, 3H), 7.91 (s, 3H), 7.92 (t, 3H)

Example 2 (Production of Compound Example T1)

The same reactions and purification as those of Example 1 were performed except that 3-(hydroxymethyl)phenylboronic acid was changed to 3-hydroxyphenylboronic acid.

Example 3 (Production of Compound Example T6)

The same reactions and purification as those of Example 1 were performed except that: 3-(hydroxymethyl)phenylboronic acid was changed to 3-(2-hydroxyethyl)phenylboronic acid; methacrylic anhydride was changed to acryloyl chloride; the temperature at which acryloyl chloride was dropped was set to 0° C.; and the reflux stirring was changed to stirring at 20° C.

Example 4 (Production of Compound Example T7)

The same reactions and purification as those of Example 1 were performed except that: 3-(hydroxymethyl)phenylboronic acid was changed to 4-(3-hydroxypropyl)phenylboronic acid; methacrylic anhydride was changed to acryloyl chloride; the temperature at which acryloyl chloride was dropped was set to 0° ° C.; and the reflux stirring was changed to stirring at 20° ° C.

Example 5 (Production of Compound Example T8)

The same reactions and purification as those of Example 1 were performed except that 3-(hydroxymethyl)phenylboronic acid was changed to 2,6-dimethyl-4-(4,4,5,5-tetramethyl-1,3,2-dioxabororan-2-yl)phenol.

Example 6 (Production of Compound Example T9)

The same reactions and purification as those of Example 3 were performed except that 3-(hydroxymethyl)phenylboronic acid was changed to 6-(hydroxymethyl)pyridine-3-boronic acid.

Example 7 (Production of Compound Example T11)

(1) Synthesis of T11 Intermediate 1 and T11 Intermediate 2

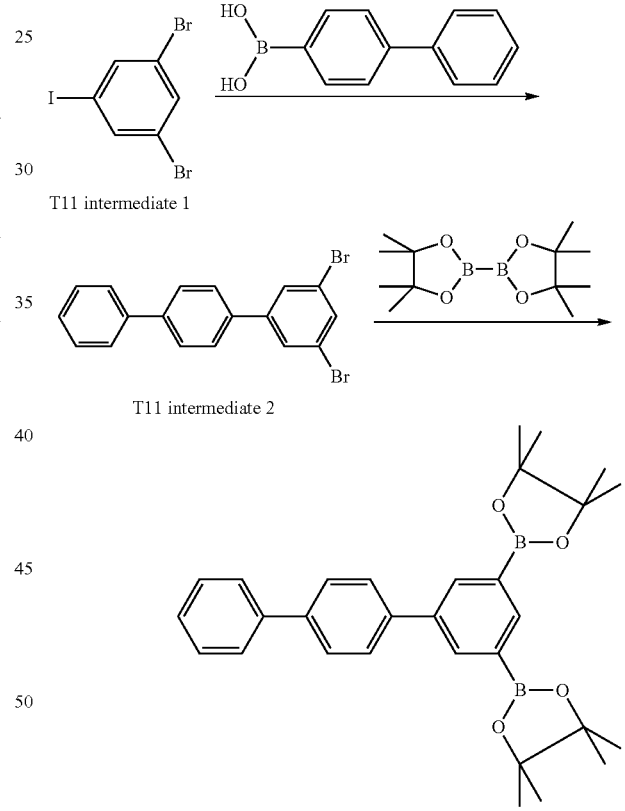

(1-1) Synthesis of T11 Intermediate 1

Under a nitrogen atmosphere, 15.0 g of 1,3-dibromo-5-iodobenzene, 17.2 g of 4-biphenylboronic acid, 26.4 g of sodium carbonate, 1,200 mL of toluene, 150 mL of ethanol, 150 mL of water, and 3.59 g of tetrakis(triphenylphosphine) palladium were sequentially added to a 3-liter three-necked flask, and were stirred for 10 hours under heating reflux at 70° C. The reaction liquid was left to cool to room temperature, and was then diluted with chloroform, followed by washing with water three times. The organic layer was dried (1-2) Synthesis of T11 Intermediate 2

Under a nitrogen atmosphere, 10.0 g of the T11 intermediate 1, 14.4 g of bis-dioxaborolane, 15.2 g of potassium acetate, 1.05 g of [1,1'-bis(diphenylphosphino)ferrocene] palladium(II) dichloride dichloromethane adduct, and 200 mL of N,N-dimethylformamide were loaded into a 500-milliliter three-necked flask, and were heated to 80° C. After that, the mixture was stirred under the temperature for 6 hours. After the mixture had been cooled to room temperature, 200 mL of water was added to the mixture, and the whole was stirred for 1 hour, followed by filtration. The resultant cake was washed with water, and the resultant crude product was purified by silica gel chromatography to provide 8.2 g of a T11 intermediate 2 (yield: 51%).

(3) Synthesis of T11 Intermediate 3

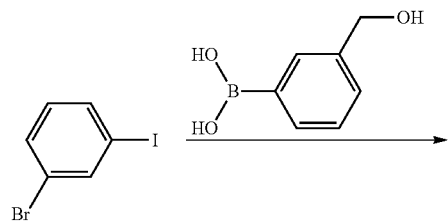

T11 intermediate 3

Under a nitrogen atmosphere, 12.0 g of 1-bromo-3-iodobenzene, 6.8 g of 3-(hydroxymethyl)phenylboronic acid, 27.0 g of sodium carbonate, 360 mL of toluene, 120 mL of ethanol, 120 mL of water, and 3.7 g of tetrakis(triphenylphosphine)palladium were sequentially added to a 1-liter three-necked flask, and were stirred for 10 hours under heating reflux at 70° C. The reaction liquid was left to cool to room temperature, and was then diluted with chloroform, followed by washing with water three times. The organic layer was dried with magnesium sulfate. The crude product obtained by removing the solvent was purified by silica gel chromatography to provide 8.2 g of a T11 intermediate 3 (yield: 73%).

(4) Synthesis of T11 Intermediate 4

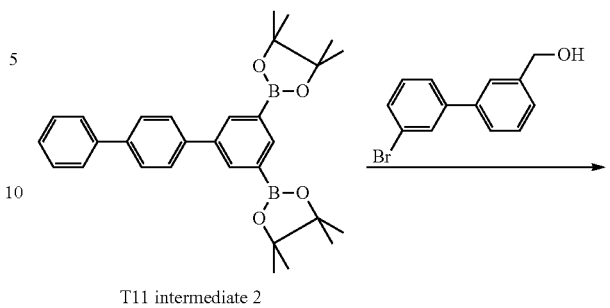

T11 intermediate 2

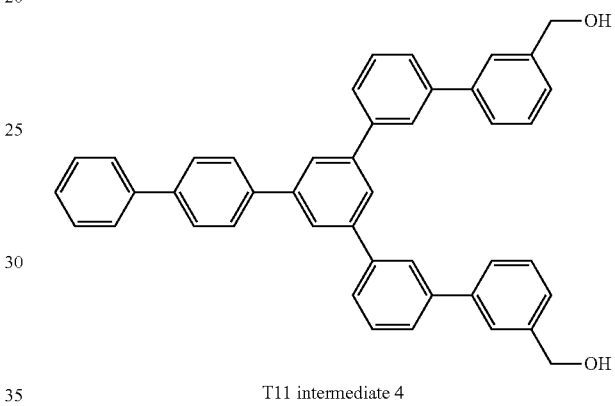

T11 intermediate 4

Under a nitrogen atmosphere, 7.0 g of the T11 intermediate 2, 8.2 g of the T11 intermediate 3, 7.6 g of sodium carbonate, 0.033 g of palladium acetate, 0.14 g of 2-dicyclohexylphosphino-2',4',6'-triisopropylbiphenyl, 210 mL of toluene, 70 mL of ethanol, and 70 mL of water were loaded into a 1,000-milliliter three-necked flask, and were refluxed and stirred for 8 hours under heating. After the heating, the mixture was left to cool to room temperature. After that, 100 mL of hexane was added to the mixture, and the whole was stirred for 1 hour, followed by filtration. The resultant cake was washed with water and hexane, and was then dissolved in acetone. 10.0 Grams of activated carbon was added to the solution, and the mixture was stirred under room temperature for 30 minutes. After that, the mixture was filtered, and the solvent of the filtrate was removed. The crude product obtained by removing the solvent was washed with ethanol and dried to provide 5.6 g of a T11 intermediate 4 (yield: 65%).

(5) Synthesis of T11

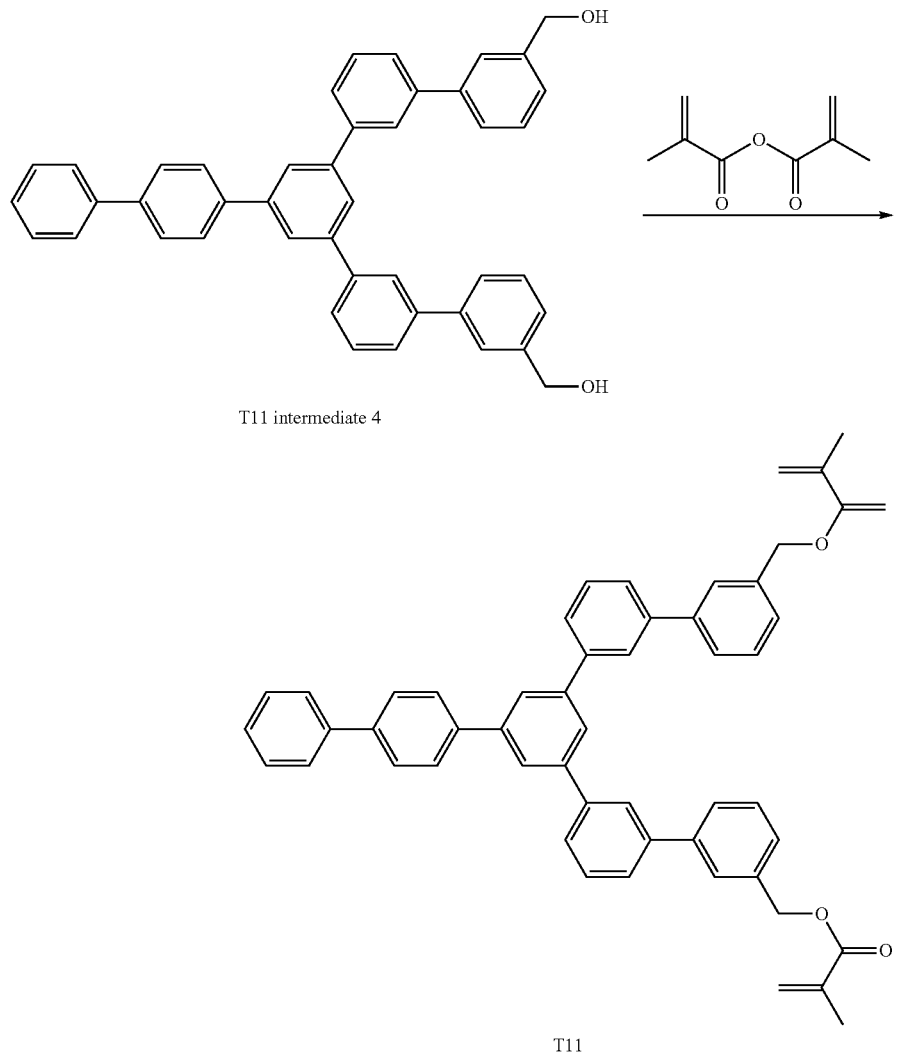

T11 intermediate 4

T11

Under a nitrogen atmosphere, 6.0 g of the T11 intermediate 4, 210 mL of tetrahydrofuran, 0.36 g of hydroquinone monomethyl ether (MEHQ), and 5.5 mL of triethylamine were loaded into a 500-milliliter three-necked flask. After that, 4.8 g of methacrylic anhydride was dropped into the flask, and the mixture was refluxed and stirred for 20 hours under heating. The reaction liquid was diluted with toluene, and the resultant organic layer was washed with acidic and basic aqueous solutions. After that, the organic layer was dried with brine and anhydrous magnesium sulfate. The crude product obtained by removing the solvent was purified by silica gel chromatography to provide 2.9 g of the T11 (yield: 42%).

Example 8 (Production of Compound Example T12)

The same reactions and purification as those of Example 7 were performed except that 4-biphenylboronic acid was changed to 2-biphenylboronic acid.

Example 9 (Production of Compound Example T16)

The same reactions and purification as those of Example 7 were performed except that 4-biphenylboronic acid was changed to 1-naphthaleneboronic acid.

Example 10 (Production of Compound Example T17)

The same reactions and purification as those of Example 7 were performed except that 4-biphenylboronic acid was changed to 2-naphthaleneboronic acid.

Example 11 (Production of Compound Example T18)

The same reactions and purification as those of Example 7 were performed except that 4-biphenylboronic acid was changed to 4-(4-biphenyl)phenylboronic acid.

Example 12 (Production of Compound Example T20)

The same reactions and purification as those of Example 7 were performed except that: 4-biphenylboronic acid and 3-(hydroxymethyl)phenylboronic acid were changed to a T20 intermediate and 5-(hydroxymethyl)pyridine-3-boronic acid, respectively; and the mass of methacrylic anhydride was increased by a factor of 1.5.

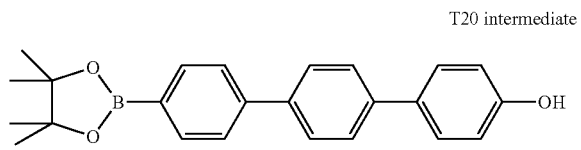 [SMILES: CC1(C)OB(c2ccc(-c3ccc(-c4ccc(O)cc4)cc3)cc2)OC1(C)C]

T20 intermediate

Example 13 (Production of Compound Example T21)

The same reactions and purification as those of Example 7 were performed except that: 4-biphenylboronic acid and the T11 intermediate 3 were changed to a T21 intermediate 1, and a mixture containing the T11 intermediate 3 and a T21 intermediate 2 at a mass ratio of 50:50, respectively; and the mass of methacrylic anhydride was increased by a factor of 1.5.

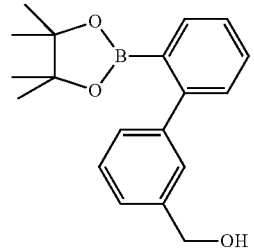

T21 intermediate 1

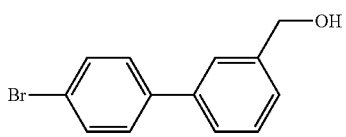

T21 intermediate 2

Example 14 (Production of Compound Example T24)

The same reactions and purification as those of Example 7 were performed except that: 4-biphenylboronic acid and the T11 intermediate 3 were changed to a T24 intermediate and a T21 intermediate 2, respectively; and the mass of methacrylic anhydride was increased by a factor of 1.5.

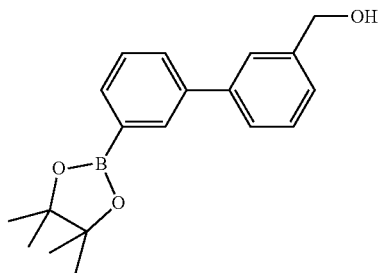

T24 intermediate

Example 15 (Production of Compound Example T25)

The same reactions and purification as those of Example 7 were performed except that: 4-biphenylboronic acid and the T11 intermediate 3 were changed to a T21 intermediate 1 and a T21 intermediate 2, respectively; and the mass of methacrylic anhydride was increased by a factor of 1.5.

Example 16 (Production of Compound Example T30)

The same reactions and purification as those of Example 7 were performed except that 4-biphenylboronic acid and the T11 intermediate 3 were changed to 3-pyridylboronic acid and a T21 intermediate 2, respectively.

Comparative Example 1

The following comparative example compound was synthesized.

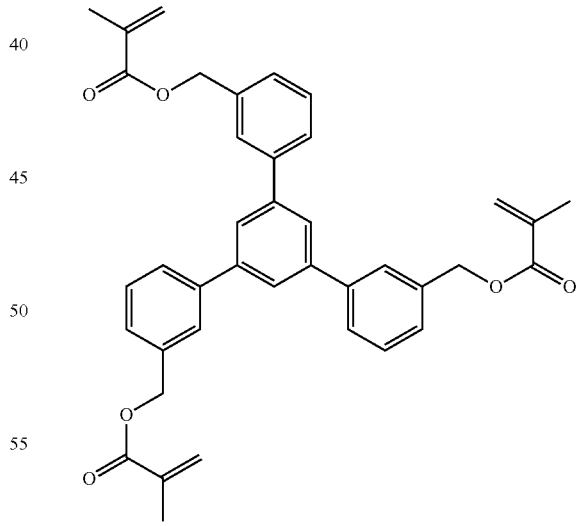

Comparative Example Compound

Evaluation

The (meth)acrylate compounds obtained in Examples and Comparative Example were subjected to the following evaluations. The results are shown in Table 4.

(1) Refractive Index Measurement

A spacer having a thickness of 300 μm, and a resin composition containing, for example, a compound serving as a measurement object, a polymerization inhibitor (methoxyphenol, manufactured by FUJIFILM Wako Pure Chemical Corporation), and a polymerization initiator (IRGACURE 184 (1-hydroxy-cyclohexyl-phenyl-ketone), manufactured by BASF SE) were mounted on high-refractive index glass having a thickness of 1 mm (S-TIH11 (product name), manufactured by HOYA Corporation). Next, quartz glass was mounted on the resin composition serving as a measurement object to press and extend the composition through the spacer so that the composition had a thickness of 300 μm. Light from a high-pressure mercury lamp (UL750 (product name), manufactured by HOYA CANDEO OPTRONICS) was applied to the sample to cure the resin composition sandwiched between the two glass substrates. After the curing, heating treatment was performed at 100° C. for 5 hours for completing the reaction. Thus, a refractive index measurement sample was produced. The refractive index of the refractive index measurement sample was measured with an Abbe refractometer (manufactured by Kalnew Optical Industrial Co., Ltd.), and was evaluated based on the following criteria. The glass substrates to be used need to have refractive indices higher than that of a cured product of the optical composition.

A: 1.65 or more

B: 1.62 or more to less than 1.65

D: Less than 1.62

(2) Transmittance Measurement

A transmittance measurement sample having a thickness of 500 μm and a transmittance measurement sample having a thickness of 300 μm were each produced in the same manner as in the section (1). The refractive index measurement sample may be used as the transmittance measurement sample having a thickness of 300 μm. The transmittance of the transmittance measurement sample of each thickness was measured with a spectrophotometer U-4000 (product name) manufactured by Hitachi High-Technologies Corporation, and was converted into an internal transmittance (500 μm) at 400 nm, followed by its evaluation based on the following criteria.

A: 85% or more

B: 80% or more to less than 85%

C: 75% or more to less than 80%

TABLE 4

| | Compound | Refractive index nd | Evaluation | Transmittance (%) 400 nm | Evaluation |
|---|---|---|---|---|---|
| Example 1 | T2 | 1.65 | A | 88 | A |
| Example 2 | T1 | 1.63 | B | 90 | A |
| Example 3 | T6 | 1.66 | A | 89 | A |
| Example 4 | T7 | 1.66 | A | 90 | A |
| Example 5 | T8 | 1.65 | A | 85 | A |
| Example 6 | T9 | 1.63 | B | 89 | A |
| Example 7 | T11 | 1.67 | A | 84 | B |
| Example 8 | T12 | 1.63 | B | 82 | B |
| Example 9 | T16 | 1.64 | B | 80 | B |
| Example 10 | T17 | 1.67 | A | 84 | B |
| Example 11 | T18 | 1.67 | A | 75 | C |
| Example 12 | T20 | 1.65 | A | 81 | B |
| Example 13 | T21 | 1.64 | B | 82 | B |

TABLE 4-continued

| | Compound | Refractive index nd | Evaluation | Transmittance (%) 400 nm | Evaluation |
|---|---|---|---|---|---|
| Example 14 | T24 | 1.69 | A | 77 | C |
| Example 15 | T25 | 1.66 | A | 77 | C |
| Example 16 | T30 | 1.67 | A | 77 | C |
| Comparative Example 1 | Comparative example compound | 1.61 | D | 90 | A |

The present disclosure is not limited to the embodiments described above, and various changes and modifications can be made without departing from the spirit and scope of the present disclosure. The following claims are appended hereto in order to make the scope of the present disclosure public.

According to the present disclosure, there can be provided the (meth)acrylate compound having a high refractive index and a high transmittance, the resin composition, the resin cured product, the optical element, and the optical apparatus each using the compound, and the hydroxy compound that is an intermediate of the compound.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A (meth)acrylate compound represented by general formula (1):

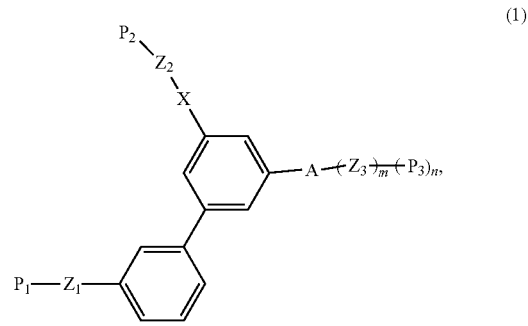

wherein in the general formula (1):

X represents a phenylene group;

$Z_1$ to $Z_3$ are each independently selected from the group consisting of a phenyl group, a heteroaryl group, a phenylene group, a heteroarylene group, a phenylalkylene group having an alkylene group having 1 to 4 carbon atoms, and a heteroaralkylene group having an alkylene group having 1 to 4 carbon atoms, where the phenyl group, the heteroaryl group, the phenylene group, the heteroarylene group, the phenylalkylene group, and the heteroaralkylene group each represented by any one of $Z_1$ to $Z_3$ may each have an alkyl group having 1 to 4 carbon atoms;

$P_1$ to $P_3$ are each independently selected from the group consisting of an acryloyloxy group and a methacryloyloxy group;

A is selected from the group consisting of an aryl group, a heteroaryl group, an arylene group, and a heteroarylene group; and m and n each represent 0 or 1, provided that when m represents 0, n represents 0.

2. The (meth)acrylate compound according to claim 1, wherein the (meth)acrylate compound is represented by general formula (2):

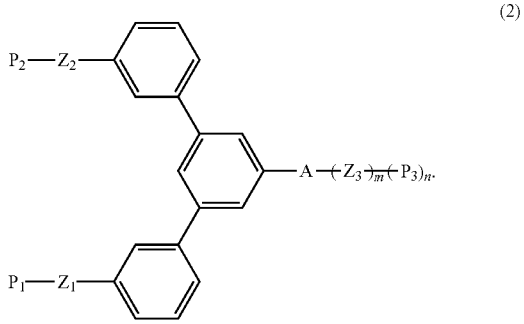

3. The (meth)acrylate compound according to claim 1, wherein the (meth)acrylate compound is represented by general formula (3):

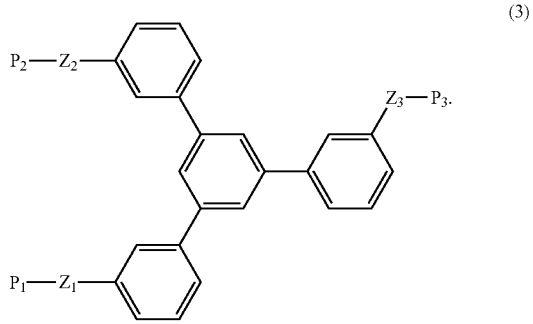

4. The (meth)acrylate compound according to claim 1, wherein the (meth)acrylate compound is represented by general formula (4):

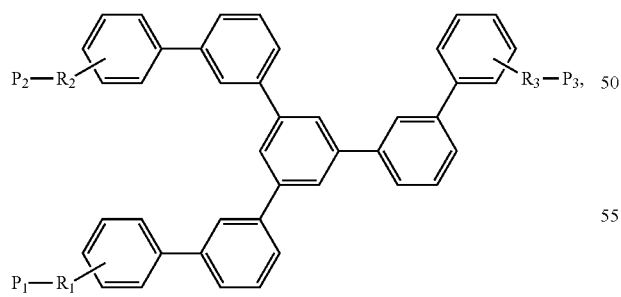

wherein, in the general formula (4), $R_1$ to $R_3$ are each independently selected from the group consisting of alkylene groups each having 1 to 4 carbon atoms.

5. A resin composition comprising the (meth)acrylate compound of claim 1.

6. A resin cured product obtained by polymerizing the resin composition of claim 5.

7. An optical element comprising:
a base material; and
the resin cured product of claim 6 arranged on the base material.

8. An optical apparatus comprising:
a housing; and
an optical system arranged in the housing, the optical system being formed of at least one of lenses,
wherein the at least one of lenses is the optical element of claim 7.

9. An image pickup apparatus comprising:
a housing;
an optical system arranged in the housing, the optical system being formed of at least one of lenses; and
an image pickup element arranged in the housing, the image pickup element being configured to receive light that has passed the optical system,
wherein the at least one of lenses is the optical element of claim 7.

10. The image pickup apparatus according to claim 9, wherein the image pickup apparatus is a camera.

11. The (meth)acrylate compound according to claim 1, wherein in the general formula (1), $Z_1$ to $Z_3$ are independently selected from a phenyl group, a phenylene group, a phenyl alkylene group having an alkylene group having 1 to 4 carbon atoms, and a heteroarylene group having an alkylene group having 1 to 4 carbon atoms, where the heteroarylene group is a divalent group excluding two hydrogen atoms among hydrogen atoms directly bonded to carbon atoms or a heteroatom constituting a pyrrole, pyridine, pyrazine, or pyrimidine ring, and where the phenyl group, the phenylene group, the phenyl alkylene group, and the heteroarylene group represented by $Z_1$ to $Z_3$ may have an alkyl group having 1 to 4 carbon atoms, and
wherein A is selected from an aryl group, a heteroaryl group, and an arylene group, where the heteroaryl group is a monovalent group derived from pyrrole, pyridine, pyrazine, or pyrimidine.

12. A (meth)acrylate compound represented by general formula (5):

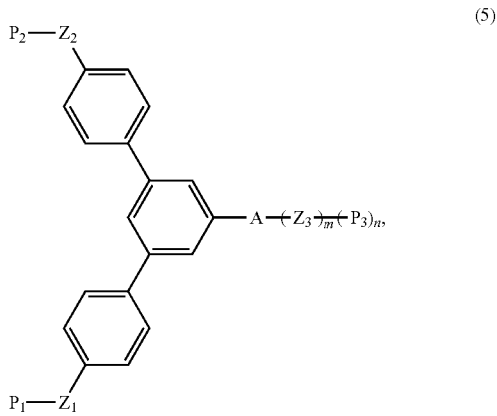

wherein, in the general formula (5):
$Z_1$ to $Z_3$ are each independently selected from the group consisting of a phenyl group, a heteroaryl group, a phenylene group, a heteroarylene group, a phenylalkylene group having an alkylene group having 1 to 4 carbon atoms, and a heteroaralkylene group having an alkylene group having 1 to 4 carbon atoms, where the phenyl group, the heteroaryl group, the phenylene group, the heteroarylene group, the phenylalkylene group, and the heteroaralkylene group each represented by any one of $Z_1$ to $Z_3$ may each have an alkyl group having 1 or more to 4 carbon atoms;

$P_1$ to $P_3$ are each independently selected from the group consisting of an acryloyloxy group and a methacryloyloxy group;

A is selected from the group consisting of an aryl group, a heteroaryl group, an arylene group, and a heteroarylene group; and m and n each represent 0 or 1, provided that when m represents 0, n represents 0.

13. The (meth)acrylate compound according to claim 12, wherein in the general formula (1), $Z_1$ to $Z_3$ are independently selected from a phenyl group, a phenylene group, a phenyl alkylene group having an alkylene group having 1 to 4 carbon atoms, and a heteroarylene group having an alkylene group having 1 to 4 carbon atoms, where the heteroarylene group is a divalent group excluding two hydrogen atoms among hydrogen atoms directly bonded to carbon atoms or a heteroatom constituting a pyrrole, pyridine, pyrazine, or pyrimidine ring, and where the phenyl group, the phenylene group, the phenyl alkylene group, and the heteroarylene group represented by $Z_1$ to $Z_3$ may have an alkyl group having 1 to 4 carbon atoms, and wherein A is selected from an aryl group, a heteroaryl group, and an arylene group, where the heteroaryl group is a monovalent group derived from pyrrole, pyridine, pyrazine, or pyrimidine.

14. A compound represented by general formula (9):

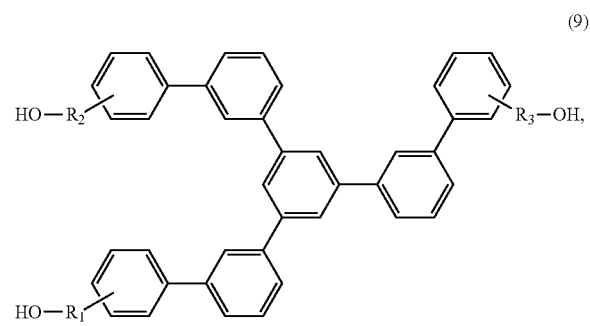

(9)

wherein, in the general formula (9), $R_1$ to $R_3$ are each independently selected from the group consisting of alkylene groups each having 1 to 4 carbon atoms.

* * * * *